US010517489B2

(12) United States Patent
Narasimhan et al.

(10) Patent No.: US 10,517,489 B2
(45) Date of Patent: Dec. 31, 2019

(54) WRIST WORN ACCELEROMETER FOR PULSE TRANSIT TIME (PTT) MEASUREMENTS OF BLOOD PRESSURE

(71) Applicant: Apple Inc., Cupertino, CA (US)

(72) Inventors: Ravi Narasimhan, Sunnyvale, CA (US); Richard C. Kimoto, Cupertino, CA (US); Thomas J. Sullivan, Cupertino, CA (US); Todd K. Whitehurst, Cupertino, CA (US); Derek Park-shing Young, Cupertino, CA (US); Zijing Zeng, Cupertino, CA (US); Erno Klaassen, Cupertino, CA (US)

(*) Notice: Subject to any disclaimer, the term of this patent is extended or adjusted under 35 U.S.C. 154(b) by 249 days.

(21) Appl. No.: 15/507,607

(22) PCT Filed: Sep. 8, 2015

(86) PCT No.: PCT/US2015/048848
§ 371 (c)(1),
(2) Date: Feb. 28, 2017

(87) PCT Pub. No.: WO2016/040263
PCT Pub. Date: Mar. 17, 2016

(65) Prior Publication Data
US 2017/0281024 A1    Oct. 5, 2017

Related U.S. Application Data

(60) Provisional application No. 62/047,472, filed on Sep. 8, 2014.

(51) Int. Cl.
*A61B 5/021*    (2006.01)
*A61B 5/11*    (2006.01)
(Continued)

(52) U.S. Cl.
CPC ............ *A61B 5/02125* (2013.01); *A61B 5/11* (2013.01); *A61B 5/681* (2013.01); *A61B 5/6824* (2013.01);
(Continued)

(58) Field of Classification Search
CPC ....... A61B 5/11; A61B 5/024; A61B 5/02125; A61B 5/022; A61B 5/0225;
(Continued)

(56) References Cited

U.S. PATENT DOCUMENTS 6,176,831 B1    1/2001 Voss et al.
6,228,034 B1    5/2001 Voss et al.
(Continued)

FOREIGN PATENT DOCUMENTS

WO    2014089665    6/2014
WO    2015193551    12/2015
WO    2016040263    3/2016

OTHER PUBLICATIONS

John Bales, Trigonometry and Vectors, http://jwbales.us/precal/part6/part6.4.html, 2012. (Year: 2012).*
(Continued)

*Primary Examiner* — Daniel L Cerioni
*Assistant Examiner* — Raymond P Dulman
(74) *Attorney, Agent, or Firm* — Kilpatrick Townsend and Stockton LLP

(57) ABSTRACT

Wrist-worn devices and related methods measure a pulse transit time non-invasively and calculate a blood pressure value using the pulse transit time. A wrist-worn device includes an accelerometer, a photo-lethysmogram (PPG) or a pulse pressure sensor, and a controller. The PPG or the pulse pressure sensor coupled to the wrist-worn device for detecting an arrival of a blood pressure pulse at the user's wrist. The controller is configured to process output signals
(Continued)

from the accelerometer to detect when the blood pressure pulse is propagated from the left ventricle of the user's heart, process a signal from the PPG or the pulse pressure sensor to detect when the blood pressure pulse arrives at the wrist, calculate a pulse transit time (PTT) for propagation of the blood pressure pulse from the left ventricle to the wrist, and generate one or more blood pressure values for the user based on the PTT.

23 Claims, 14 Drawing Sheets

(51) Int. Cl.
*A61B 5/00* (2006.01)
*A61B 5/024* (2006.01)

(52) U.S. Cl.
CPC ............ *A61B 5/024* (2013.01); *A61B 5/02416* (2013.01); *A61B 5/1102* (2013.01)

(58) Field of Classification Search
CPC ............ A61B 5/02255; A61B 5/02405; A61B 5/02416; A61B 5/02422; A61B 5/0245; A61B 5/025; A61B 5/681; A61B 5/1102
USPC .................................. 600/481, 483, 485–503
See application file for complete search history.

(56) References Cited

U.S. PATENT DOCUMENTS

| | | | |
|---|---|---|---|
| 6,443,906 B1 | 9/2002 | Ting et al. | |
| 6,514,211 B1 | 2/2003 | Baura | |
| 6,554,774 B1 | 4/2003 | Miele | |
| 6,676,600 B1 | 1/2004 | Conero et al. | |
| 6,705,990 B1 | 3/2004 | Gallant et al. | |
| 6,730,038 B2 | 5/2004 | Gallant et al. | |
| 6,918,879 B2 | 7/2005 | Ting et al. | |
| 6,932,772 B2 | 8/2005 | Kan | |
| 6,974,419 B1 | 12/2005 | Voss et al. | |
| 7,048,691 B2 | 5/2006 | Miele et al. | |
| 7,144,372 B2 | 12/2006 | Ng et al. | |
| 7,291,112 B2 | 11/2007 | Martin et al. | |
| 7,317,409 B2 | 1/2008 | Conero | |
| 7,318,807 B2 | 1/2008 | Ng | |
| 7,361,147 B2 | 4/2008 | Ng | |
| 7,503,896 B2 | 3/2009 | Miele et al. | |
| 7,503,897 B2 | 3/2009 | Ng et al. | |
| 7,867,170 B2 | 1/2011 | Gallant et al. | |
| 7,871,381 B2 | 1/2011 | Ng et al. | |
| 7,871,382 B2 | 1/2011 | Ng | |
| 7,946,994 B2 | 5/2011 | Finburgh et al. | |
| 7,976,471 B2 | 7/2011 | Martin et al. | |
| 8,157,730 B2 | 4/2012 | Leboeuf et al. | |
| 8,204,786 B2 | 6/2012 | Leboeuf et al. | |
| D666,169 S | 8/2012 | Tucker et al. | |
| 8,251,903 B2 | 8/2012 | Leboeuf et al. | |
| 8,323,982 B2 | 12/2012 | LeBoeuf et al. | |
| 8,328,727 B2 | 12/2012 | Miele et al. | |
| 8,469,895 B2 | 6/2013 | Ting et al. | |
| 8,506,497 B2 | 8/2013 | Katayama et al. | |
| 8,512,242 B2 | 8/2013 | Leboeuf et al. | |
| 8,597,195 B2 | 12/2013 | Gallant et al. | |
| 8,647,270 B2 | 2/2014 | Leboeuf et al. | |
| 8,652,040 B2 | 2/2014 | Leboeuf et al. | |
| 8,652,409 B2 | 2/2014 | LeBoeuf et al. | |
| 8,657,753 B2 | 2/2014 | Ting et al. | |
| 8,672,854 B2 | 3/2014 | Mccombie et al. | |
| 8,700,111 B2 | 4/2014 | Leboeuf et al. | |
| 8,702,607 B2 | 4/2014 | Leboeuf et al. | |
| 8,777,862 B2 | 7/2014 | Finburgh et al. | |
| 8,788,002 B2 | 7/2014 | LeBoeuf et al. | |
| 2008/0146890 A1 | 6/2008 | LeBoeuf et al. | |
| 2008/0146892 A1 | 6/2008 | Leboeuf et al. | |
| 2008/0220535 A1 | 9/2008 | LeBoeuf et al. | |
| 2009/0112071 A1 | 4/2009 | LeBoeuf et al. | |
| 2010/0160798 A1 | 6/2010 | Banet et al. | |
| 2010/0324384 A1 | 12/2010 | Moon et al. | |
| 2011/0066043 A1* | 3/2011 | Banet ..................... A61B 5/022 |
| | | | 600/485 |
| 2011/0213254 A1 | 9/2011 | Ting | |
| 2013/0059396 A1 | 3/2013 | LeBoeuf et al. | |
| 2013/0131519 A1 | 5/2013 | LeBoeuf et al. | |
| 2013/0304112 A1 | 11/2013 | Ting et al. | |
| 2014/0114147 A1 | 4/2014 | Romesburg | |
| 2014/0128690 A1 | 5/2014 | LeBoeuf | |
| 2014/0135596 A1 | 5/2014 | LeBoeuf et al. | |
| 2014/0140567 A1 | 5/2014 | LeBoeuf et al. | |
| 2014/0163399 A1 | 6/2014 | Gallant et al. | |
| 2014/0171755 A1 | 6/2014 | LeBoeuf et al. | |
| 2014/0171762 A1 | 6/2014 | LeBoeuf et al. | |
| 2014/0180039 A1 | 6/2014 | LeBoeuf et al. | |
| 2014/0187941 A1* | 7/2014 | Shusterman ....... A61B 5/02116 |
| | | | 600/438 |
| 2014/0200415 A1 | 7/2014 | McCombie et al. | |
| 2015/0112606 A1 | 4/2015 | He et al. | |
| 2015/0164351 A1 | 6/2015 | He et al. | |
| 2015/0316579 A1* | 11/2015 | Pakzad .................. G01P 15/02 |
| | | | 702/150 |
| 2015/0374256 A1* | 12/2015 | Skrabal ................ A61B 5/0408 |
| | | | 600/301 |
| 2016/0041531 A1* | 2/2016 | Mackie ................ A61B 5/0059 |
| | | | 368/80 |
| 2016/0220152 A1* | 8/2016 | Meriheina ............ A61B 5/1102 |
| 2016/0278646 A1* | 9/2016 | Hu ............................ A61B 5/11 |
| 2017/0143216 A1* | 5/2017 | Oksala ............... A61B 5/02125 |
| 2017/0238847 A1* | 8/2017 | Inan ................... A61B 5/02125 |

OTHER PUBLICATIONS

London, et al., Influence of arterial pulse and reflected waves on blood pressure and cardiac function, Sep. 1999, American Heart Journal, vol. 138, 3, Part 2, p. S220-S223 (Year: 1999).*

"National, State, and Local Area Vaccination Coverage Among Children Aged 19-35 Months—United States, 2011", Morbidity Mortality Weekly Report Weekly, vol. 61 No. 35, Sep. 7, 2012, 24 pages.

"Non-invasive haemodynamic monitor", BioZ® Cardio Profile, 42 pages.

"Prevention, Detection, Evaluation, and Treatment of High Blood Pressure", National High Blood Pressure Education Program, The Seventh Report of the Joint National Committee, 2004, 104 pages.

"Pulse Transit Time and Velocity Calculation", Biopac Systems, Inc., Mar. 21, 2006, 3 pages.

Allen , "Photoplethysmography and its application in clinical physiological measurement", Physiol. Meas. vol. 28, 2007, pp. R1-R39.

Ashraf et al., "Size of radial and ulnar artery in local population", J Pak Med Assoc, vol. 60, No. 10, Oct. 2010, pp. 817-819.

Baheti et al., "An ultra low power pulse oximeter sensor based on compressed sensing", Body Sensor Networks, IEEE, 2009, pp. 144-148.

Cattivelli et al., "Noninvasive Cuffless Estimation of Blood Pressure from Pulse Arrival Time and Heart Rate with Adaptive Calibration", IEEE Computer Society, 2009, pp. 114-119.

Couceiro et al., "Characterization of Surrogate Parameters for Blood Pressure Regulation in Neurally-Mediated Syncope", 2013 35th Annual International Conference of the IEEE Engineering in Medicine and Biology Society (EMBC), 2013, pp. 5381-5385.

Critchley , "Minimally Invasive Cardiac Output Monitoring in the Year 2012", Artery Bypass, Mar. 13, 2013, pp. 45-80.

Cybulski et al., "Impedance Cardiography", Lecture Notes in Electrical Engineering, 2011, pp. 7-37.

Czajkowski et al., "Long-term Plan for Research and Translation in Hypertension for Enhancing Public Health", National Heart, Lung, and Blood Institute, National Institutes of Health Department of Health and Human Services, Dec. 2004, 77 pages.

Da Silva , "A pervasive system for real-time blood pressure Monitoring", Feb. 13, 2013, pp. 1-23.

(56) References Cited

OTHER PUBLICATIONS

Douniama, "Blood Pressure Estimation based on Pulse Transit Time and Compensation of Vertical Position", 3rd Russian-Bavarian Conference on Bio-Medical Engineering, 2007, 5 pages.
Douniama et al., "Blood Pressure Tracking Capabilities of Pulse Transit Times in Different Arterial Segments: A Clinical Evaluation", Computers in Cardiology, vol. 36, 2009, pp. 201-204.
Fagard, "Exercise characteristics and the blood pressure response to dynamic physical training", Med. Sci. Sports Exerc., vol. 33, No. 6,, 2001, pp. S484-S492.
Forouzanfar et al., "Coefficient-Free Blood Pressure Estimation Based on Pulse Transit Time-Cuff Pressure Dependence", IEEE Transactions on Biomedical Engineering, vol. 60, No. 7, Jul. 2013, pp. 1814-1824.
Gesche et al., "Continuous blood pressure measurement by using the pulse transit time: comparison to a cuff-based method", Eur J Appl Physiol, May 10, 2011, 7 pages.
Gesche et al., "Continuous blood pressure measurement by using the pulse transit time: comparison to a cuff-based method", Eur J Appl Physiol, vol. 112, 2012, pp. 309-315.
Harrison et al., "Portable acoustic myography—a realistic noninvasive method for assessment of muscle activity and coordination in human subjects in most home and sports settings", Physiological Reports ISSN 2051-817X, vol. 1, Iss.2, e00029, 2013, pp. 1-9.
Harwood-Smith et al., "Assessment of pulse transit time to indicate cardiovascular changes during obstetric spinal anaesthesia", British Journal of Anaesthesia, vol. 96 (1), 2006, pp. 100-105.
Hassan et al., "Non-invasive Continuous Blood Pressure Monitoring Based on PWTT", Journal of Advanced Computer Science and Technology Research, vol. 1, 2011, pp. 63-73.
He et al., "Evaluation of the Correlation Between Blood Pressure and Pulse Transit Time", IEEE, 2013, 4 pages.
Hennig et al., "Continuous blood pressure measurement using pulse transit time", Somnologie vol. 17, Jun. 6, 2013, pp. 104-110.
Hsiu et al., "Correlation of Harmonic Components between the Blood Pressure and Photoplethysmography Waveforms Following Local-Heating Stimulation", International Journal of Bioscience, Biochemistry and Bioinformatics, vol. 2, No. 4, Jul. 2012, pp. 248-253.
Hsiu et al., "Effects of Local-Heating Stimulation on the Harmonic Structure of the Blood Pressure and Photoplethysmography Waveforms", 2nd International Conference on Biomedical Engineering and Technology IPCBEE vol. 34, 2012, pp. 1-5.
Huotari et al., "Photoplethysmography and its detailed pulse waveform analysis for arterial stiffness", Rakenteiden Mekaniikka (Journal of Structural Mechanics), vol. 44, No. 4, 2011, pp. 345-362.
Jeong et al., "Continuous Blood Pressure Monitoring using Pulse Wave Transit Time", ICCAS, 2005, 4 pages.
Jobbagy, "Blood Pressure Measurement: Assessment of a Variable Quantity", 2010, pp. 316-324.
Kado et al., "RedTacton Near-body Electric-field Communications Technology and Its Applications", NTT Technical Review, vol. 8 No. 3, 2010, pp. 1-6.
Kalsi, "Design of Arterial Blood Pressure, Heart Rate Variability, and Breathing Rate Monitoring Device", Electrical and Biomedical Engineering Design Project (4BI6), Apr. 23, 2009, 65 pages.
Kim, "Design of Infrared Sensor Based Measurement System for Continuous Blood Pressure Monitoring Device", pp. 1-12.
Kim et al., "Development of an Arterial Tonometer Sensor", 31st Annual International Conference of the IEEE EMBS, Sep. 2-6, 2009, pp. 3771-3774.
Lima et al., "Use of Peripheral Perfusion Index Derived From the Pulse Oximetry Signal as a Noninvasive Indicator of Perfusion", Crit Care Med., vol. 30(6), 2002, 10 pages.
Marcinkevics et al., "Relationship between arterial pressure and pulse wave velocity using photoplethysmography during the post-exercise recovery period", Acta Universitatis Latviensis, vol. 753, Biology,, 2009, pp. 59-68.
Marinkovic, "Reconstructing the Blood Pressure Waveform using a Wearable Photoplethysmograph Sensor and Hydrostatic Pressure Variations Measured by Accelerometers", Submitted to the Department of Mechanical Engineering in Partial Fulfillment of the Requirements for the Degrees of Master of Science in Mechanical Engineering at the Massachusetts Institute of Technology, Feb. 2007, 54 pages.
Matthys et al., "Long-term pressure monitoring with arterial applanation tonometry: a non-invasive alternative during clinical intervention?", Technol Health Care, vol. 16, 2008, pp. 183-193.
McCarthy et al., "An examination of calibration intervals required for accurately tracking blood pressure using pulse transit time algorithms", Journal of Human Hypertension, 2013, pp. 1-7.
McCarthy, "An Investigation of Pulse Transit Time as a Non-Invasive Blood Pressure Measurement Method", Journal ofPhysics:ConferenceSeries. vol. 307, 2011, 6 pages.
McCombie et al., "Adaptive hydrostatic blood pressure calibration: Development of a wearable, autonomous pulse wave velocity blood pressure monitor", Proceedings of the 29th Annual International Conference of the IEEE EMBS, Aug. 23-26, 2007, pp. 370-373.
Meigas et al., "Continuous Blood Pressure Monitoring Using Pulse Wave Delay", 2001, 5 pages.
Nakamura et al., "Collaborative Processing of Wearable and Ambient Sensor System for Blood Pressure Monitoring", Sensors, 11, ISSN 1424-8220 www.mdpi.com/journal/sensors, 2011, pp. 6760-6770.
Norris et al., "AgeChangesinHeartRateandBloodPressure ResponsestoTiltingandStandardizedExercise", Circulation, vol. VIII, Downloaded from http://circ.ahajournals.org/ at Cons California Dig Lib, Aug. 26, 2013, pp. 521-526.
O'Brien, "European Society of Hypertension International Protocol revision 2010 for the validation of blood pressure measuring devices in adults", Blood Pressure Monitoring, vol. 15, 2010, pp. 23-28.
O'Brien et al., "Working Group on Blood Pressure Monitoring of the European Society of Hypertension International Protocol for validation of blood pressure measuring devices in adults", Blood Pressure Monitoring, vol. 7, 2002, pp. 3-17.
O'Brien, "The British Hypertension Society protocol for the evaluation of automated and semiautomated blood pressure measuring devices with special reference to ambulatory systems", Journal of Ambulatory Monitoring, vol. 4, No. 3,, 1991, pp. 207-228.
Payne et al., "Pulse transit time measured from the ECG: an unreliable marker of beat-to-beat blood pressure", J Appl Physiol vol. 100, Sep. 1, 2005, pp. 136-141.
Proenca et al., "Is Pulse Transit Time a good indicator of Blood Pressure changes during short physical exercise in a young population?", 32nd Annual International Conference of the IEEE EMBS, Aug. 31-Sep. 4, 20, pp. 598-601.
Raissuni et al., "Can We Obtain a Noninvasive and Continuous Estimation of Cardiac Output? Comparison Between Three Noninvasive Methods", Int Heart J, Nov. 2013, pp. 395-400.
Reisner et al., "Utility of the Photoplethysmogram in Circulatory Monitoring", Anesthesiology, vol. 108, 2008, pp. 950-958.
Sackl-Pietsch et al., "Continuous non-invasive arterial pressure shows high accuracy in comparison to invasive intra-arterial blood pressure measurement", pp. 1-5.
Seo, "Evaluation of cardiac output using nonuniform hybrid electrical impedance model based on forward lumped parameter and both-hands impedance measurement system", The Graduate School Yonsei University, Department of Biomedical Engineering, Feb. 2012, 146 pages.
Shaltis et al., "A Finite Element Analysis of Local Oscillometric Blood Pressure Measurements", Proceedings of the 29th Annual International Conference of the IEEE EMBS, Aug. 23-26, 2007, pp. 355-358.
Shaltis et al., "A hydrostatic pressure approach to cuffless blood pressure monitoring", Proceedings of the 26th Annual International Conference of the IEEE EMBS, Sep. 1-5, 2004, pp. 2173-2176.
Shaltis et al., "Calibration of the Photoplethysmogram to Arterial Blood Pressure: Capabilities and Limitations for Continuous Pressure Monitoring", Proceedings of the 2005 IEEE Engineering in Medicine and Biology 27th Annual Conference, Sep. 1-4, 2005, pp. 3970-3973.

(56) References Cited

OTHER PUBLICATIONS

Shaltis et al., "Cuffless Blood Pressure Monitoring Using Hydrostatic Pressure Changes", IEEE Transactions on Biomedical Engineering, vol. 55, No. 6,, Jun. 2008, pp. 1775-1777.
Shaltis et al., "Monitoring of Venous Oxygen Saturation Using a Novel Vibratory Oximetry Sensor", 2d Joint Conference of the IEEE Engineering in Medicine and Biology, Society and the Biomedical Engineering Society, Oct. 23-26, 2002, pp. 1722-1723.
Shaltis et al., "Wearable, Cuff-less PPG-Based Blood Pressure Monitor with Novel Height Sensor", Proceedings of the 28th IEEE EMBS Annual International Conference, Aug. 30-Sep. 3, 2006, pp. 908-911.
Silverberg, "The unsupported arm: a cause of falsely raised blood pressure readings", British Medical Journal, Nov. 19, 1977, p. 1331.
Sinha et al., "Non-Invasive Blood Pressure Monitor: Beat to Beat", Technology Development Article, BARC Newsletter, Issue No. 328, Sep.-Oct. 2012, pp. 62-68.
Smith et al., "Pulse transit time: an appraisal of potential clinical applications", Thorax vol. 54, Available online at: http://thorax.bmj.com/content/54/5/452. full.html, Oct. 13, 2013, pp. 452-458.
Sola et al., "Continuous non-invasive blood pressure estimation", Diss. ETH. No. 20093, 2011, 196 pages.
Sola et al., "Noninvasive and Nonocclusive Blood Pressure Estimation via a Chest Sensor", IEEE Transactions on Biomedical Engineering, vol. 60, No. 12, Dec. 2013, pp. 3505-3513.
Sola et al., "Non-invasive monitoring of central blood pressure by electrical impedance tomography: first experimental evidence", Med Biol Eng Comput, vol. 49, 2011, pp. 409-415.
Somnomedics, "Non-invasive, continuous and non-reactive blood pressure measurement using PTT", Medical Devices for Sleep Diagnostics and Therapy, 2012, pp. 1-20.
Song et al., "Estimation of Blood Pressure Using Photoplethysmography on the Wrist", Computers in Cardiology, vol. 36, 2009, pp. 741-744.
Sorvoja et al., "Noninvasive Blood Pressure Measurement Methods", Molecular and Quantum Acoustics, vol. 27, 2006, pp. 239-264.
Spulak et al., "Experiments With Blood Pressure Monitoring Using ECG and PPG", Czech Technical University in Prague, 5 pages.
Spulak et al., "Parameters for Mean Blood Pressure Estimation Based on Electrocardiography and Photoplethysmography", Czech Technical University in Prague, 4 pages.
Teja, "Calculation of Blood Pulse Transit Time from PPG", Department of Biotechnology and Medical Engineering National Institute of Technology, Rourkela 2012, 2012, 54 pages.
Theodor et al., "Implantable Acceleration Plethysmography for Blood Pressure Determination", 35th Annual International Conference of the IEEE EMBS, Jul. 3-7, 2013, pp. 4038-4041.
Thompson et al., "Arteriosclerosis, Thrombosis, and Vascular Biology", Arterioscler Thromb Vase Biol. vol. 23, American Heart Association, Available online at: http://atvb.ahajournals.org/, 2003, pp. e42-e49.
Townsend, "Oscillometry", Medical Electronics, Michaelmas Term, 2001, pp. 48-54.
Van Dijk et al., "Oscillometry and applanation tonometry measurements in older individuals with elevated levels of arterial stiffness", Analytical methods and statistical analysis, Blood Pressure Monitoring vol. 18 No. 6, 2013, pp. 332-338.
Vignon-Clementel et al., "A Coupled Multidomain Method for Computational Modeling of Blood Flow", A Dissertation Submitted to the Department of Mechanical Engineering and The Committee on Graduate Studies of Stanford University in Partial Fulfillment of the Requirements for the Degree of Doctor of Philosophy, Jun. 2006, 207 pages.
Ward, "Blood Pressure Measurement", Cont Edu Anaesth Crit Care & Pain. vol. 7(4), 2007, pp. 122-126.
Wibmer et al., "Pulse transit time and blood pressure during cardiopulmonary exercise tests", Physiological Research Pre-Press Article, 2014, 26 pages.
Wikipedia, "Continuous noninvasive arterial pressure", Available online at: http://en.wikipedia.org/wiki/Continuous_noninvasive_arterial_pressure, Jul. 24, 2013, 8 pages.
Woidtke, "Pulse Transit Time and Peripheral Arterial Tonometry", 33 pages.
Wong et al., "An Evaluation of the Cuffless Blood Pressure Estimation Based on Pulse Transit Time Technique: a Half Year Study on Normotensive Subjects", Cardiovasc Eng. vol. 9, 2009, pp. 32-38.
Wong et al., "The Relationship between Pulse Transit Time and Systolic Blood Pressure on Individual Subjects after Exercises", Proceedings of the 1st Distributed Diagnosis and Home Healthcare (D2H2) Conference, Apr. 2-4, 2006, pp. 37-38.
Ye et al., "Estimation of Systolic and Diastolic Pressure using the Pulse Transit Time", World Academy of Science, Engineering and Technology 43 2010 726, 2010, pp. 726-731.
Yong, "A computational system to optimise noise rejection in photoplethysmography signals during motion or poor perfusion states", Med Biol Eng Comput vol. 44, 2006, pp. 140-145.
Yoon et al., "Non-constrained Blood Pressure Monitoring Using ECG and PPG for Personal Healthcare", J Med Syst. vol. 33, 2009, pp. 261-266.
Zhang, "Cuff-Free Blood Pressure Estimation Using Signal Processing Techniques", Thesis for the degree of Master of Science in the Division of Biomedical Engineering University of Saskatchewan http://hdl.handle.net/10388/etd-09082010-164956, Aug. 2010, 73 pages.
Zhang et al., "Pulse arrival time is not an adequate surrogate for pulse transit time as a marker of blood pressure", J Appl Physiol vol. 111, 2011, pp. 1681-1686.

\* cited by examiner

WRIST WORN ACCELEROMETER FOR PULSE TRANSIT TIME (PTT) MEASUREMENTS OF BLOOD PRESSURE

CROSS-REFERENCES TO RELATED APPLICATIONS

The present application is a U.S. National Stage application of PCT/US2015/048848 filed Sep. 8, 2015; which claims the benefit of U.S. Provisional Appln. No. 62/047,472 filed Sep. 8, 2014; the full disclosures of which are incorporated herein by reference in their entirety for all purposes.

BACKGROUND

Elevated blood pressure (a.k.a. hypertension) is a major risk factor for cardiovascular disease. As a result, blood pressure measurement is a routine task in many medical examinations. Timely detection of hypertension can help inhibit related cardiovascular damage via accomplishment of effective efforts in treating and/or controlling the subject's hypertension.

A person's blood pressure is a continuously changing vital parameter. As a result, sporadic office blood pressure measurements may be insufficient to detect some forms of hypertension. For example, hypertension can occur in a pattern that evades detection via isolated office blood pressure measurement. Common hypertension patterns include white coat hypertension (elevated only during a limited morning period of time), borderline hypertension (fluctuating above and below definitional levels over time), nocturnal hypertension (elevated only during sleeping hours), isolated systolic hypertension (elevated systolic pressure with non-elevated diastolic pressure), and isolated diastolic hypertension (elevated diastolic pressure with non-elevated systolic pressure). To detect such hypertension patterns, it may be necessary to perform additional blood pressure measurements over time to obtain a more complete view of a person's blood pressure characteristics. Although continuous measurement of blood pressure can be achieved by invasive means, for example, via an intra-arterial pressure sensing catheter, noninvasive blood pressure measurement approaches are more typically used.

Current noninvasive blood pressure measurement approaches include ambulatory and home blood pressure measurement strategies. These strategies provide such a more complete view of a person's blood pressure characteristics and are often employed in recommended situations. Ambulatory blood pressure measurement is performed while the person performs daily life activities. Currently, ambulatory blood pressure measurements are typically performed every 20 to 30 minutes using brachial oscillometric blood pressure measurement cuffs. Ambulatory blood pressure measurement may be recommended where the is large variability in office blood pressure measurements, where a high office blood pressure measurement is made in a person with otherwise low cardiovascular risk, when office and home blood pressure measurements vary, where resistance to drug treatment of blood pressure is noted or suspected, where hypotensive episodes are suspected, or where preclampsia is suspected in pregnant women. Home blood pressure measurement include isolated self-measurements performed by a person at home. Home blood pressure measurements may be recommended where information is desired regarding the effectiveness of blood pressure lowering medication over one or more dose-to-dose intervals and/or where doubt exists as to the reliability of ambulatory blood pressure measurement.

Current ambulatory and home blood pressure measurement approaches, however, fail to provide continuous measurement of blood pressure. Additionally, when an oscillometric blood pressure measurement cuff is used to monitor a person's blood pressure when sleeping, the intermittent inflation and deflation of the cuff can disturb the person's sleeping pattern, thereby harming the subject to some extent and potentially changing the person's sleeping blood pressure. Thus, convenient and effective approaches for noninvasive continuous measurement of blood pressure remain of interest.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Wrist-worn devices and related methods are provided for noninvasive measurement of blood pressure of a subject. In many embodiments, the wrist-worn device includes an accelerometer for detecting when blood pressure pulse begins propagating from the subject's left ventricle and a photo-plethysmogram (PPG) or a pulse pressure sensor coupled with the wrist-worn device to detect arrival of the blood pressure pulse at the subject's wrist. A pulse transit time (PTT) is calculated for the blood pulse's propagation from the left ventricle to the wrist. The PTT is used to generate one or more blood pressure values for the subject. The blood-pressure measurement approach used is noninvasive and non-occlusive and therefore suitable for both ambulatory and home blood pressure measurement and can be used to continuously monitor blood pressure over a desired period of time.

Thus, in one aspect, a wrist-worn device is provided for determining a pressure of blood within a cardiovascular system of a user. The user's cardiovascular system includes a heart. The user's wrist is covered with skin. The wrist-worn device includes an accelerometer, a photo-plethysmogram (PPG) or a pulse pressure sensor, and a controller. The accelerometer is coupled to the wrist-worn device for detecting when a blood pressure pulse is propagated from a left ventricle of the user's heart. The PPG or the pulse pressure sensor is coupled to the wrist-worn device and configured to detect an arrival of the blood pressure pulse at the user's wrist. The controller is configured to: 1) process output signals from the accelerometer to detect when the blood pressure pulse begins propagation from the left ventricle of the user's heart, 2) process a signal from the PPG or the pulse pressure sensor to detect when the blood pressure pulse arrives at the wrist, 3) calculate a pulse transit time (PTT) for propagation of the blood pressure pulse from the left ventricle to the wrist, and 4) generate one or more blood pressure values for the user based on the PTT. The wrist-worn device can include an elongate band that extends around the wrist when the device is worn by the user and non-invasively engages the skin on the wrist of the user.

The accelerometer can be configured to measure accelerations in one or more suitable directions for any suitable subsequent processing to detect when the blood pressure pulse begins propagation from the user's left ventricle. For example, the accelerometer can be configured to measure accelerations in one, two, or three directions. The wrist-worn device can include a memory to store acceleration data corresponding to accelerations measured over a recording time period for subsequent processing. The wrist-worn device can include a bandpass filter coupled with the accelerometer output signals to process and remove noise from the output signals of the accelerometer. For example, a bandpass filter that attenuates frequencies less than about 0.3 Hz and greater than about 10 Hz can be used to process the accelerometer output to remove acceleration noise outside a frequency range of interest. The controller can be configured to calculate combined acceleration magnitude values from the measured accelerations. The controller can be configured to process the combined acceleration magnitude values to detect when the blood pressure pulse is propagated from the left ventricle of the user's heart. The combined acceleration magnitudes values can be based on a combination of the measured accelerations in at least two directions. For example, an eigenvector-based principle component analysis of the measured accelerations can be used to calculate the combined acceleration magnitude values so as to reflect increased variability relative to the measured accelerations.

Processing output from the accelerometer to detect when the blood pressure pulse begins propagation from the left ventricle of the user's heart can include using the detected time when the pulse arrives at the user's wrist to select a candidate time period within the recording time period to select the acceleration data to evaluate to identify when the blood pressure pulse begins propagation from the user' left ventricle. When the acceleration data within the candidate time period is consistent with two or more blood pressure pulses propagated from the left ventricle, a time when a blood pressure pulse is propagated from the left ventricle closest to a target time within the candidate time period can be selected for the PTT calculation. Any suitable candidate time period can be used. For example, the candidate time period can be from about 100 ms to about 300 ms before the detected time when the pulse arrives at the user's wrist.

The signal from the PPG or the pulse pressure sensor can be processed using any suitable bandpass filter to remove noise. For example, the signal from the PPG or the pulse pressure sensor can be processed using a bandpass filter attenuates frequencies less than about 0.3 Hz and greater than about 10 Hz.

The signal from the PPG or the pulse pressure sensor can be processed so as to enhance detection of the arrival time of the pressure pulse to the wrist prior to the arrival of a reflection of the pressure pulse to the wrist. For example, the signal from the PPG or the pulse pressure sensor can be differentiated with respect to time. The differentiated signal can then be evaluated to select an arrival time of the pressure pulse to the wrist prior to the arrival of a reflection of the pressure pulse to the wrist.

In embodiments employing a PPG sensor, the PPG sensor can be configured to detect the arrive of the blood pressure pulse a greater depth into the wrist as compared to conventional PPG sensors. For example, the PPG sensor can include a light source and a plurality of light detectors. At least two of the light detectors can be disposed at different distances from the light source so to enable detection of different mean penetration depths of light emitted by the light source. The controller can be configured to process output from the light detectors to determine the amount of light returned from a deeper penetration depth relative to the detected mean penetration depths. At least two of the light detectors can be disposed in a range of 2 mm to 6 mm from the light source. The PPG sensor can include at least two light sources configured to emit different wavelengths of light so as to enable detection of a plurality of mean penetration depths for light emitted by the light sources. For example, the at least two light sources can include at least two of an infra-red light source, a red light source, or a green light source. The different wavelengths of light emitted can include a first wavelength of about 525 nm and a second wavelength of about 940 nm. The controller can be configured to process output from the detectors to determine the amount of light returned from a deeper penetration depth relative to the detected mean penetration depths. The PPG sensor can include both multiple light sources and multiple light detectors disposed at different distances from one or more of the light sources.

The greater detection depth can be used to monitor a deeper layer and/or a deeper artery within the wrist. For example, the controller can be configured to process signals from the light detectors to detect when the blood pressure pulse arrives at the deep blood plexus (DBP) layer at the user's wrist. The PPG sensor can non-invasively engage the skin of the user's wrist over a radial artery and be configured to detect when the blood pressure pulse arrives at the user's wrist within the user's radial artery. The controller can be configured to process signals from the light detectors to detect when the blood pressure pulse arrives at the user's wrist within the user's radial artery.

The PPG sensor can be configured to detect levels of vasomotion (e.g., vasodilation, vasoconstriction) of the user's arteries. For example, the controller can be configured to process one or more signals from the light detectors to determine a tone of the user's blood vessels. The blood pressure value generated for the user can be further based on the determined tone of the user's blood vessels.

A pulse pressure sensor can be used instead of, or in combination with, the PPG sensor. In embodiments employing a pulse pressure sensor, the pulse pressure sensor can be configured to detect the arrival of the blood pressure pulse at the user's wrist and can include at least one pressure transducer, accelerometer, or strain gauge positioned over a radial artery of the wrist of the user.

The generation of the one or more blood pressure values can be further based on an estimated elevation difference between the wrist-worn device and the user's heart so as to account for hydrostatic elevation differences in blood pressure within the user. For example, the controller can be configured to generate the estimated elevation difference based on pressure signals from one or more pressure sensors coupled to the wrist-worn device or an estimated arm posture derived from output signals from the accelerometer.

The wrist-worn device can include any suitable combination of the features described herein. For example, the wrist-worn device can include any of the combinations of features recited in the claims included herein.

In another aspect, a method is provided for determining a pressure of blood within a cardiovascular system of a user. The user's cardiovascular system includes a heart. The user's wrist is covered by skin. The method includes: 1) detecting, with an accelerometer of a wrist-worn device non-invasively engaging an anterior surface of the wrist of the user, a first signal indicative of when blood is ejected from the left ventricle of the subject's heart; 2) detecting, with a PPG or a pulse pressure sensor of the wrist-worn device non-invasively engaging the skin on the wrist of the user, a second signal indicative when a blood pressure pulse corresponding to the blood ejection arrives at the wrist; 3) calculating a pulse transit time (PTT) for the blood pressure pulse from the ejection of the blood from the left ventricle to arrival of the blood pressure pulse at the wrist; and 4) generating one or more relative blood pressure values for the subject based on the PTT. The method can include detecting when the accelerometer is positioned on the user' chest.

The method can include storing acceleration data corresponding to the accelerometer output for a recording time period. The detected arrival time of the blood pressure pulse at the wrist can be used to select a candidate time period within the recording time period to select the acceleration data to evaluate to identify when the blood is ejected from the left ventricle. When the evaluation of the selected acceleration data identifies two or more candidate times for when the blood is ejected from the left ventricle within the candidate time period, one of the candidate times closest to a target time within the candidate time period can be selected for the PTT calculation. Any suitable candidate time period can be used. For example, the candidate time period can be from about 100 ms to about 300 ms before the detected time when the pulse arrives at the user's wrist.

The method can include processing the accelerometer output with any suitable bandpass filter to remove noise. For example, the accelerometer output can be processed using a bandpass filter that attenuates frequencies less than about 0.3 Hz and greater than about 10 Hz.

The method can include processing the PPG or pressure sensor output with any suitable bandpass filter to remove noise. For example, the PPG or pressure sensor output can be processed using a bandpass filter attenuates frequencies less than about 0.3 Hz and greater than about 10 Hz.

The method can include processing the signal from the PPG or the pulse pressure sensor so as to enhance detection of the arrival time of the pressure pulse to the wrist prior to the arrival of a reflection of the pressure pulse to the wrist. For example, the signal from the PPG or the pulse pressure sensor can be differentiated with respect to time. The differentiated signal can then be evaluated to select an arrival time of the pressure pulse to the wrist prior to the arrival of a reflection of the pressure pulse to the wrist.

The method can include measuring accelerations in two or more directions. For example, the accelerometer output can include accelerations measured in three directions. The method can include calculating combined acceleration magnitude values from the measured accelerations. The combined acceleration magnitudes values can be based on a combination of the measured acceleration in at least two directions. The method can include processing the combined acceleration magnitude values to detect when blood is ejected from the left ventricle of the user's heart. The method can include performing an eigenvector-based principle component analysis of the measured accelerations to calculate the combined acceleration magnitude values so as to reflect increased sensitivity to blood ejections from the left ventricle.

The method can include processing output from the PPG sensor to determine a tone of the subject's blood vessels. The one or more blood pressure values generated for the subject can be further based on the determined tone of the subject's blood vessels.

The generation of the one or more blood pressure values can be further based on calibration data including measured blood pressure values and corresponding PTTs for the subject. For example, an oscillometric blood pressure measurement cuff can be used to measure one or more blood pressure values for the subject at or at about the same time as when the method is used to calculate a corresponding one or more PTTs for the subject. Suitable calibration data can then be formulated using the oscillometric blood pressure measurement cuff measured blood pressure values and the corresponding one or more PTTs for the subject using known approaches. For example, a least squares method can be used to determine a suitable equation for blood pressure of the subject as a function of PTT. As another example, a suitable equation for blood pressure of the subject as a function of PTT can be predefined using any suitable approach, such as by entering coefficients of the equation or selecting a predefined equation based on one or more characteristics of the subject (e.g., age of the subject, whether the subject is male or female, and/or height to waist diameter of the subject).

The method can further include calculating trending data for a time period based on the one or more relative blood pressure values. Any suitable time period can be used, for example, one or more days, one or more weeks, one or more months, or one or more years.

The method can further include transmitting the one or more relative blood pressure measurements and/or the trending data to a suitable device. For example, the one or more blood pressure measurements and/or the trending data can be transmitted to a mobile device, table, computer, or database.

The method can further include detecting different mean penetration depths of light emitted by the PPG sensor by at least one of: a) using at least two light detectors disposed at different distances from a light source of the PPG sensor; and b) using a plurality of light sources configured to emit different wavelengths of light. The method can include processing output from the light detectors to determine the amount of light returned from a deeper penetration depth relative to detected mean penetration depths.

The method can further include processing one or more signals from the PPG sensor to detect when the blood pressure pulse corresponding to the ejected blood arrives at a selected depth and/or location at the wrist. For example, the method can include processing one or more signals from the PPG sensor to detect when the blood pressure pulse corresponding to the ejected blood arrives at the deep blood plexus (DBP) layer at the subject's wrist. As another example, the method can include processing one or more signals from the PPG sensor to detect when the blood pressure pulse corresponding to the ejected blood arrives at the subject's wrist within the subject's radial artery.

The method can include estimating an elevation difference between the wrist-worn device and the user's heart so as to account for hydrostatic elevation differences in blood pressure within the user. For example, the estimated elevation difference can be based on output from one or more pressure sensors or an estimated arm posture derived from output from the accelerometer.

The method can include any suitable combination of the acts and/or features described herein. For example, the method can include any of the combinations of acts and/or features recited in the claims included herein.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
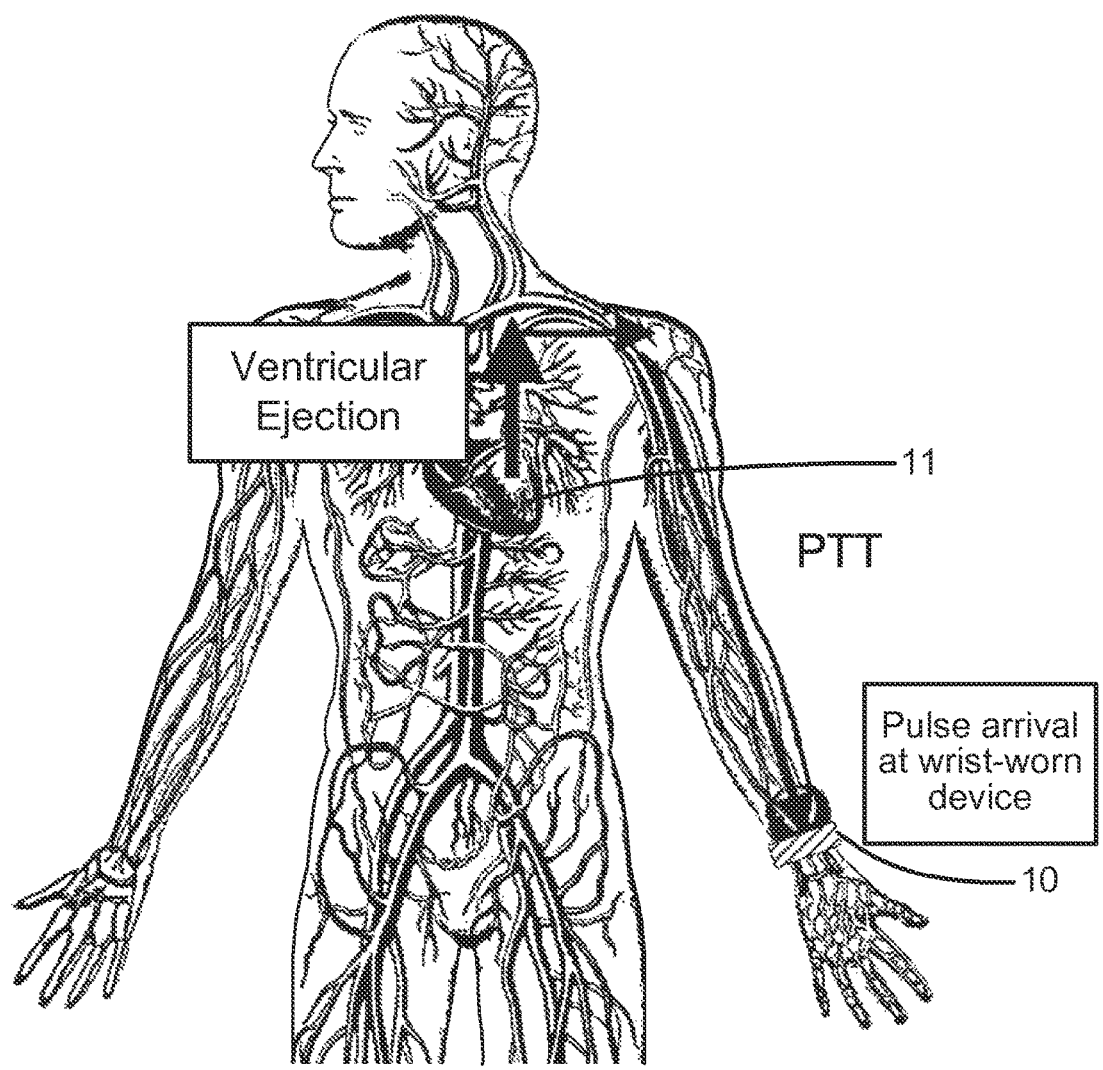
FIG. 1 illustrates a propagation path of a blood pressure pulse from the left ventricle to a wrist on which a wrist-worn blood pressure measurement device is worn, in accordance with many embodiments.

Referring now to the drawings, in which like reference numerals represent like parts throughout the several views, FIG. 1 illustrates a propagation path of a blood pressure pulse from ejection from the left ventricle of a subject's heart to a wrist on which a wrist-worn blood-pressure measurement device 10 is worn, in accordance with many embodiments. The wrist-worn device 10 is configured to detect when the blood corresponding to the blood pressure pulse is ejected from a subjects heart 12 and when the blood pressure pulse arrives at the wrist-worn device 10. The wrist-worn device 10 is configured to calculate a pulse transit time (PTT) for the blood pressure pulse for the transit of the blood pressure pulse from the left ventricle to the wrist-worn device 10. The determined PTT is then used to determine one or more blood-pressure values for the subject.

In general, PTT is the time it takes for a pulse pressure wave to propagate through a length of a subject's arterial tree. PTT has a nonlinear relationship with blood pressure. Factors that can impact how fast a blood pressure pulse will travel at a given blood-pressure in a particular artery, include, for example, arterial stiffness, arterial wall thickness, and arterial inner diameter. Equation (1) provides a functional relationship between PTT and mean arterial blood pressure (MAP).

$$MAP = \frac{1}{\alpha} \ln\left[\frac{\rho D (\Delta d)^2}{h E_0 (PTT)^2}\right] \quad (1)$$

where: MAP is mean arterial blood pressure;
PTT is Pulse Transit Time;
h is arterial wall thickness,
D is artery diameter;
$\rho$ is density of blood;
$E_0$ is the Young's modulus of the artery at zero pressure;
$\alpha$ is a subject dependent physiological constant; and
$\Delta d$ is the arterial distance between the subjects left ventricle and the wrist.

The pressure pulse travels through different arteries during its transit from the left ventricle to the wrist. As a result, variation in corresponding variables in equation (1), for example, arterial wall thickness (h), artery diameter (D), and Young's modulus of the artery at zero pressure ($E_0$), will change the relationship between blood pressure and how fast the blood pressure pulse travels through the respective artery. Each blood pressure pulse, however, will travel through the same arteries during transit from the left ventricle to the wrist. Accordingly, a relationship between the overall PTT from the left ventricle to the wrist and MAP can be given by replacing arterial wall thickness (h), artery diameter (D), and Young's modulus of the artery at zero pressure ($E_0$) with respective effective values suitable for the combination of all the arteries through which the pressure pulse travels from the left ventricle to the wrist. Therefore, equation (1) can be simplified to the relationship given below in equation (2).

$$MAP = \frac{1}{\alpha} \ln\left[\frac{K}{(PTT)^2}\right] \quad (2)$$

$$\text{where: } K = \frac{\rho D (\Delta d)^2}{h E_0}$$

is suitable for the subject and the arterial tree segment over which PTT is being measured.

The values of (K) and ($\alpha$) can be determined using any suitable approach. For example, an oscillometric blood pressure measurement cuff can be used to measure one or more blood pressure values for the subject at or at about the same time as when corresponding one or more PTTs are determined for the subject via the wrist-worn device 10. Suitable calibration data can then be formulated using the oscillometric blood pressure measurement cuff measured blood pressure values and the corresponding one or more PTTs for the subject using known approaches. For example, a least squares method can be used to determine suitable values or relationships for determining the values of (K) and (α).

A similar approach can be used to predict MAP, systolic blood pressure (SBP), and diastolic blood pressure (DBP) values based on a measured PTT value. For example, equations (3), (4), and (5) are example regression equations that can be used to predict MAP, SBP, and DBP, respectively, from a measured PTT.

$$MAP = K_{MAP} \times [\log(PTT) - \log(PTT_0)] + MAP_{BASELINE} \quad (3)$$

where: MAP is predicted mean arterial blood pressure;
$MAP_{BASELINE}$ is a baseline measured MAP;
$K_{MAP}$ is a subject dependent constant for MAP;
PTT is the measured pulse transit time; and
$PTT_0$ is the measured pulse transit time for $MAP_{BASELINE}$.

$$SBP = K_{SBP} \times [\log(PTT) - \log(PTT_0)] + SBP_{BASELINE} \quad (4)$$

where: SBP is predicted systolic blood pressure;
$SBP_{BASELINE}$ is a baseline measured systolic blood pressure;
$K_{SBP}$ is a subject dependent constant for systolic blood pressure;
PTT is the measured pulse transit time; and
$PTT_0$ is the measured pulse transit time for $SBP_{BASELINE}$.

$$DBP = K_{DBP} \times [\log(PTT) - \log(PTT_0)] + DBP_{BASELINE} \quad (5)$$

where: DBP is predicted diastolic blood pressure;
$DBP_{BASELINE}$ is a baseline measured diastolic blood pressure;
$K_{DBP}$ is a subject dependent constant for diastolic blood pressure;
PTT is the measured pulse transit time; and
$PTT_0$ is the measured pulse transit time for $DBP_{BASELINE}$.

Figure 2:
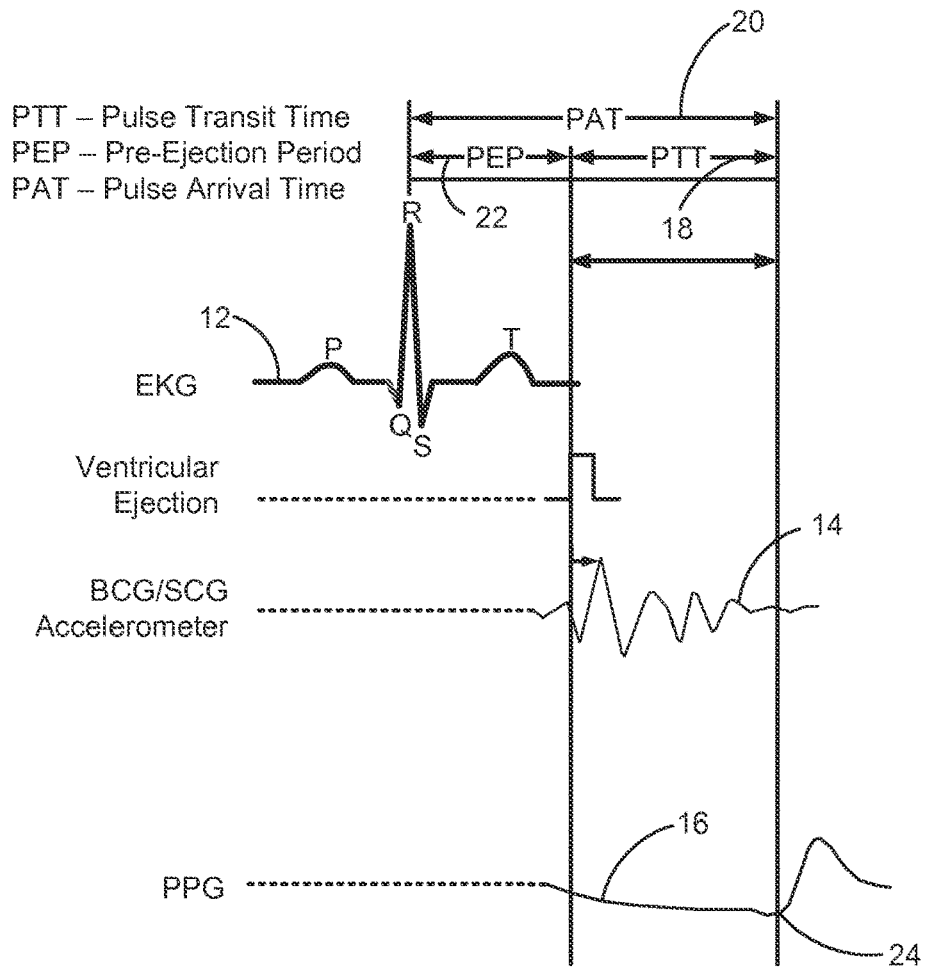
FIG. 2 illustrates accelerometer and PPG signals relative to a pulse transit time (PIT) for a blood pressure pulse propagating from the left ventricle to a wrist on which a blood pressure measurement device is worn, in accordance with many embodiments.

FIG. 2 shows an electrocardiogram (EKG) trace segment 12, a Ballisto-Cardiogram (BCG) or Seismo-Cardiogram (SCG) trace segment 14, and a PPG signal 16 relative to a pulse transit time (PTT) 18 for a blood pressure pulse between the left ventricle of the subject to the wrist-worn device 10. In many embodiments, the wrist-worn device 10 includes an accelerometer and a PPG or a pulse pressure sensor. The accelerometer measures one or more accelerations used to generate a BCG and/or a SCG, which can be processed to identify when the blood pressure pulse originates from the subject's left ventricle. A PPG sensor is used to generate a PPG signal for the subject. The EKG trace segment 12 is shown for reference in describing the operation of the heart. The EKG trace segment 12 has a segment (QRS) known as the QRS complex, which reflects the rapid depolarization of the right and left ventricles. The prominent peak (R) of the EKG trace corresponds to beginning of contraction of the left ventricle. A pulse arrival time (PAT) 20 is the time between the peak (R) of the EKG trace and arrival of the blood pressure pulse at the wrist-worn device 10. As the left ventricle contracts, pressure builds within the left ventricle to a point where the pressure exceeds pressure in the aorta thereby causing the aortic valve to open. A pre-ejection period (PEP) 22 is the time period between the peak (R) of the EKG trace and the opening of the aortic valve. The PEP 22 correlates poorly with blood pressure. The BCG/SCG trace 14 can be processed to identify when the aortic valve opens. The ejection of blood from the left-ventricle into the aorta results in an associated acceleration of the chest cavity that is detected via the accelerometer included in the wrist-worn device 10. In many embodiments, the arrival of the blood pressure pulse is detected via the PPG signal 16, which includes an inflection point 24 that occurs upon arrival of the blood pressure pulse to the wrist-worn device 10.

Figure 3:
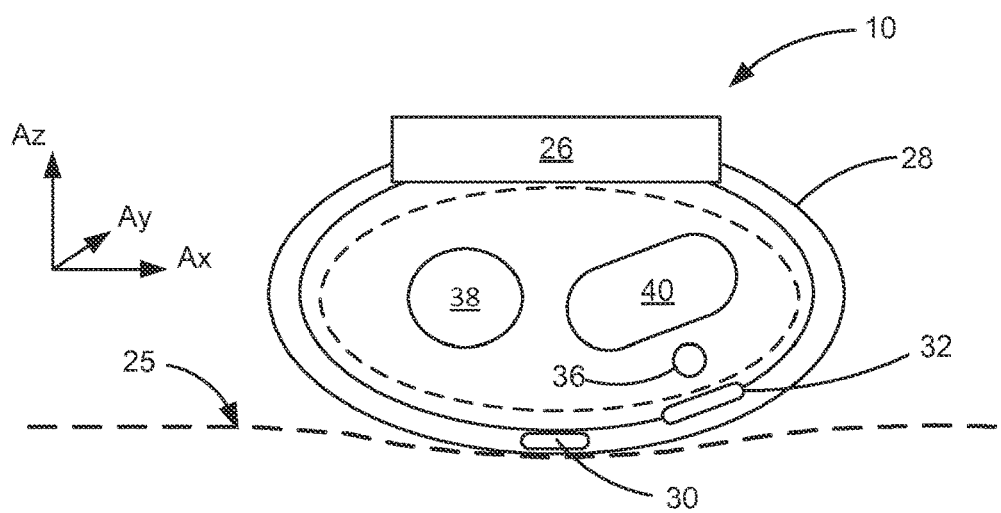
FIG. 3 is a schematic side view of a wrist-worn blood pressure measurement device held in contact with a user's chest, in accordance with many embodiments.

FIG. 3 shows a schematic side view of the wrist-worn device 10 held in contact with a user's chest 25, in accordance with many embodiments. When the wrist-worn device 10 is held in contact with a user's chest, SCG data is generated. When the wrist-worn device 10 is not held in contact with a user's chest, BCG data is generated. The wrist-worn device 10 includes a main unit 26, a wrist-worn elongate band 28, an accelerometer 30, and a PPG sensor 32. The accelerometer 30 and the PPG sensor 32 are supported on the wrist-worn elongate band 28 and operatively connected with the main unit 26. The PPG sensor 32 is positioned and oriented to interface with a wrist 34 of the user when the device 10 is worn on the wrist 34. The main unit 26 includes circuitry and/or software for processing output from the accelerometer 30 and the PPG sensor 32 so as to measure a PTT and calculate one or more blood pressure values for the subject based on the PTT. In the illustrated embodiment, the PPG sensor 32 is located on the wrist-worn band 28 so as to be disposed to sense the arrival of the blood-pressure pulse within a radial artery 36 of the subject. Cross sections of the ulna bone 38 and the radius bone 40 of the subject are shown for reference. In described embodiments, the accelerometer 30 is oriented to measure accelerations in each of axes Ax and Ay (in the plane of the user's chest 25) and axis Az (which is perpendicular to the user's chest 25).

Figure 4:
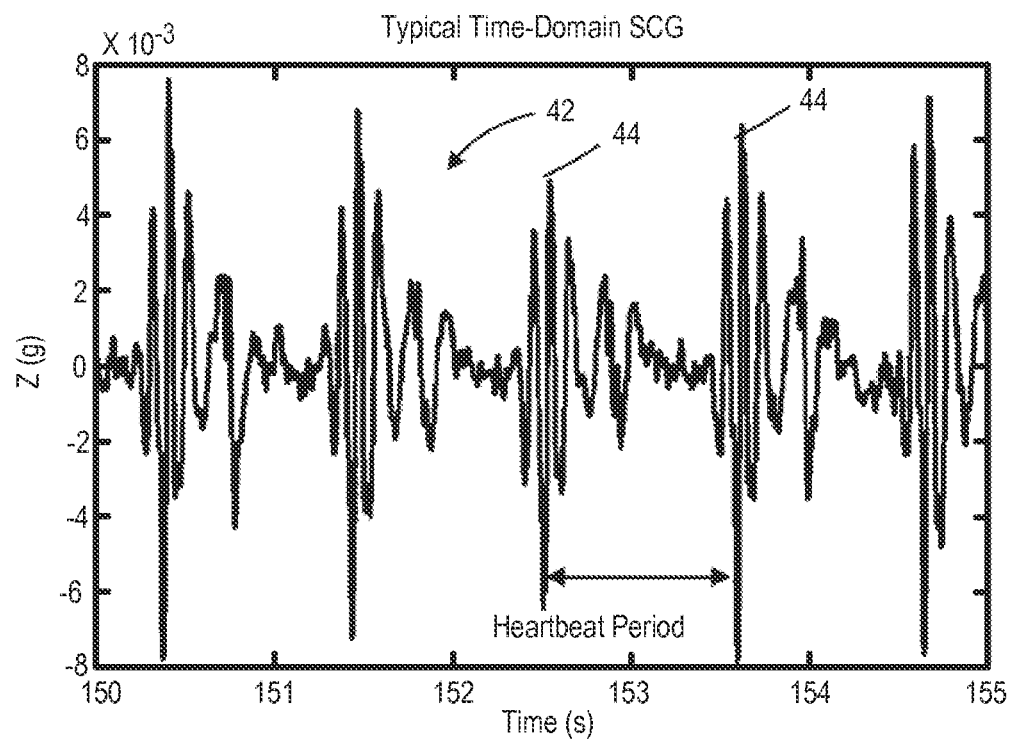
FIG. 4 is a typical time-domain trace of a measured Seismo-Cardiogram acceleration oriented normal to a user's chest surface, in accordance with many embodiments.

FIG. 4 shows a typical time-domain SCG trace 42 for acceleration measured in a direction normal to a user's chest surface, in accordance with many embodiments. The SCG trace 42 has localized peaks 44, which correspond to the opening of the aortic valve and associated ejection of blood into the aorta from the user's left ventricle. The SCG trace 42 can be processed to identify the localized peaks 44 and the associated time points at which the localized peaks occur, thereby identifying one or more time points for one or more ejections of blood from the left ventricle into the user's aorta. The identified one or more time points can be used in conjunction with one or more time points when the respective blood pressure pulses arrive at the wrist as detected by the PPG sensor 32 or alternatively via a pulse pressure sensor to calculate a PTT for the propagation of the blood pressure pulse from the left ventricle to the user's wrist. The calculated PTT can then be used to generate one or more blood pressure values for the user as described herein.

Figure 5:
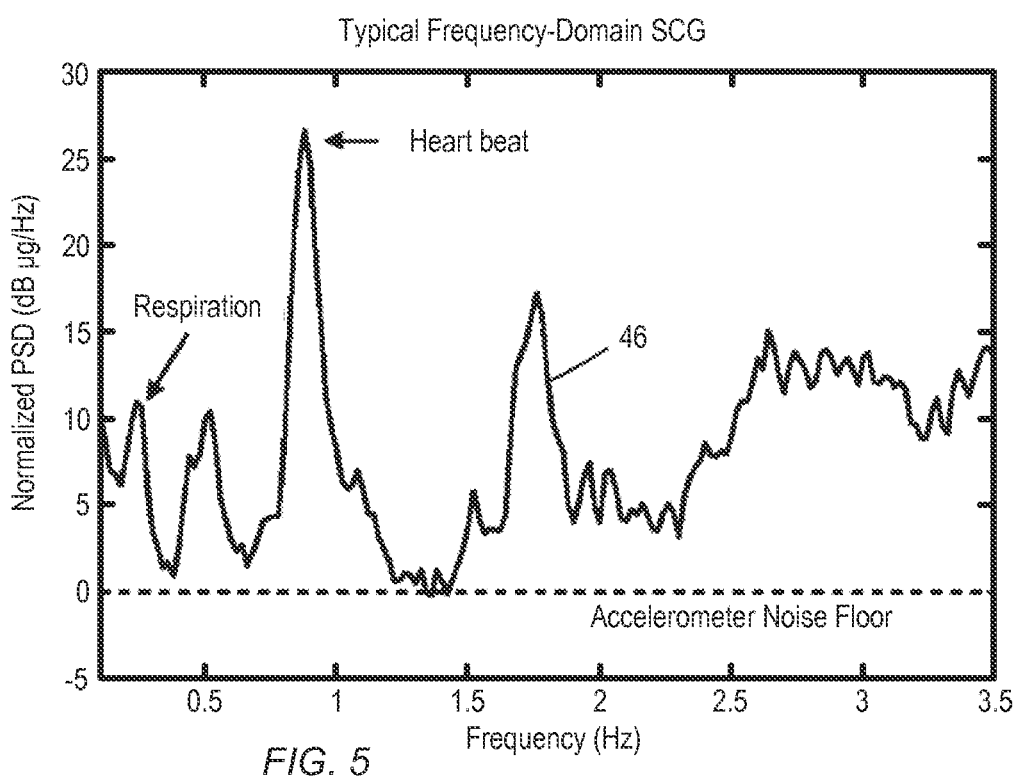
FIG. 5 is a typical frequency-domain Seismo-Cardiogram, in accordance with many embodiments.
Figure 6:
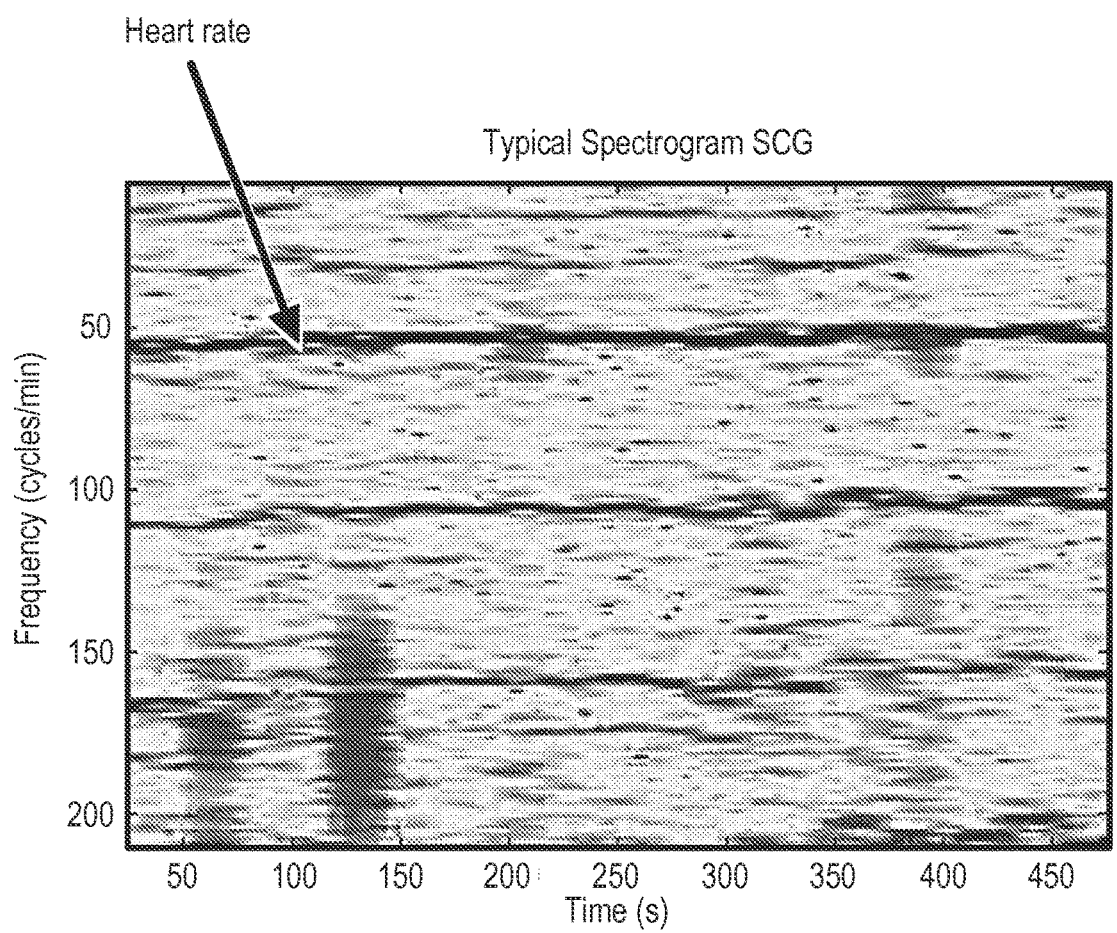
FIG. 6 is a typical spectrogram Seismo-Cardiogram, in accordance with many embodiments.

FIGS. 5 and 6 show additional plots that can be generated from output of the accelerometer 30. FIG. 5 shows a typical frequency-domain SCG 46 generated from the output of an accelerometer held in contact with a user's chest. The frequency-domain SCG, which can be used to identify heart rate for the user, which can be used to double check that the time points corresponding to the localized peaks 44 are separated by a time interval consistent with the identified heart rate. FIG. 6 shows a typical spectrogram SCG, which can also be used to identify heart rate for the user.

Figure 7:
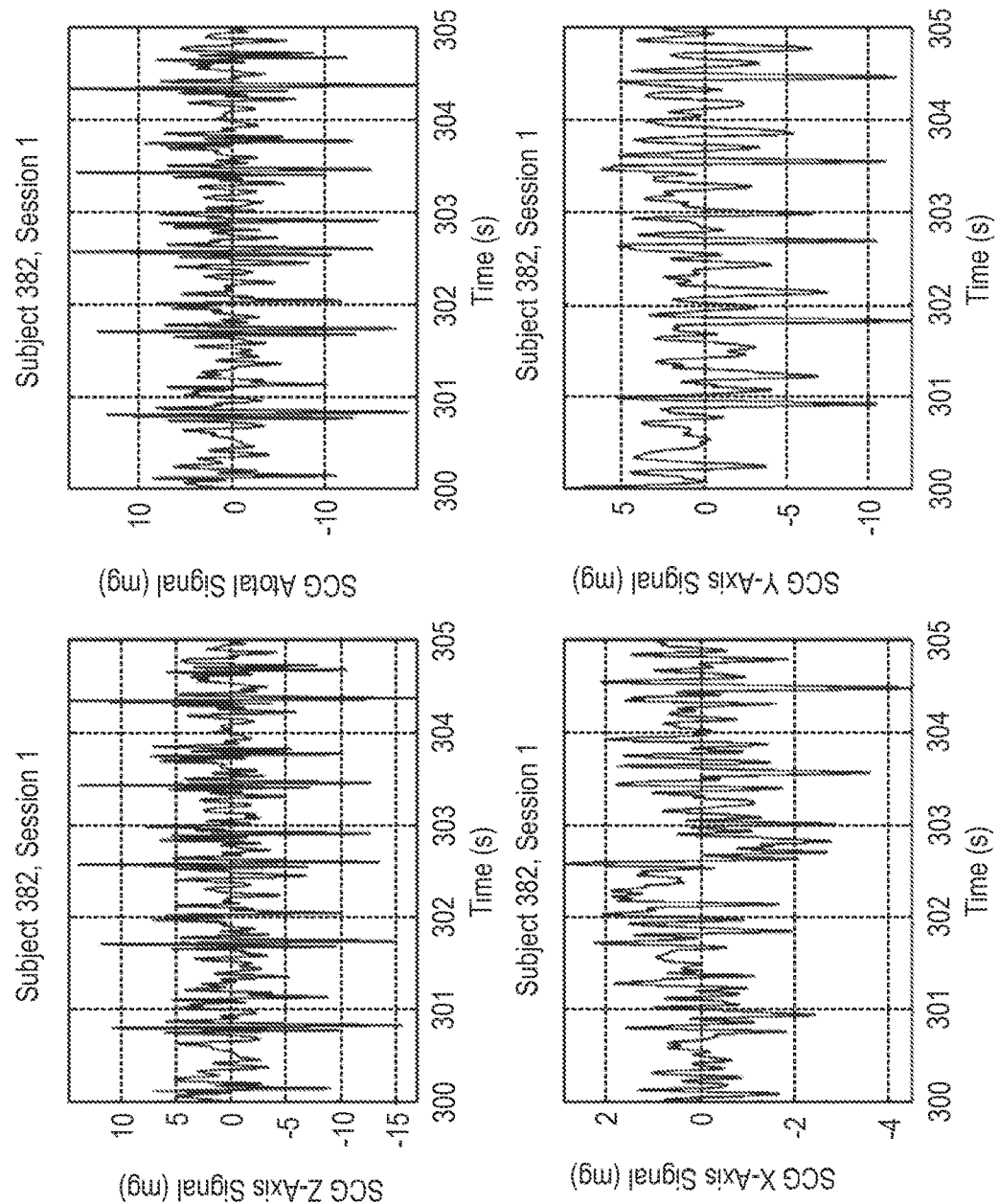
FIG. 7 shows x-axis acceleration, y-axis acceleration, z-axis acceleration, and vector-sum acceleration Seismo-Cardiogram plots, in accordance with many embodiments.

FIG. 7 shows example x-axis acceleration, y-axis acceleration, z-axis acceleration, and vector-sum acceleration SCG plots measured using an accelerometer held in contact with a subject's chest. Each of the z-axis acceleration (normal to the subject's chest) and the vector-sum acceleration (Atotal) exhibits clear acceleration peaks corresponding to respective ejections of blood from the subject's left ventricle. The y-axis acceleration (in plane of the subject's chest) is relatively less clear with respect to having acceleration peaks corresponding to respective ejections of blood from the subject's left ventricle. And the x-axis acceleration (also in plane with the subject's chest) is the least clear with respect to having acceleration peaks corresponding to respective ejections of blood from the subject's left ventricle.

Figure 8:
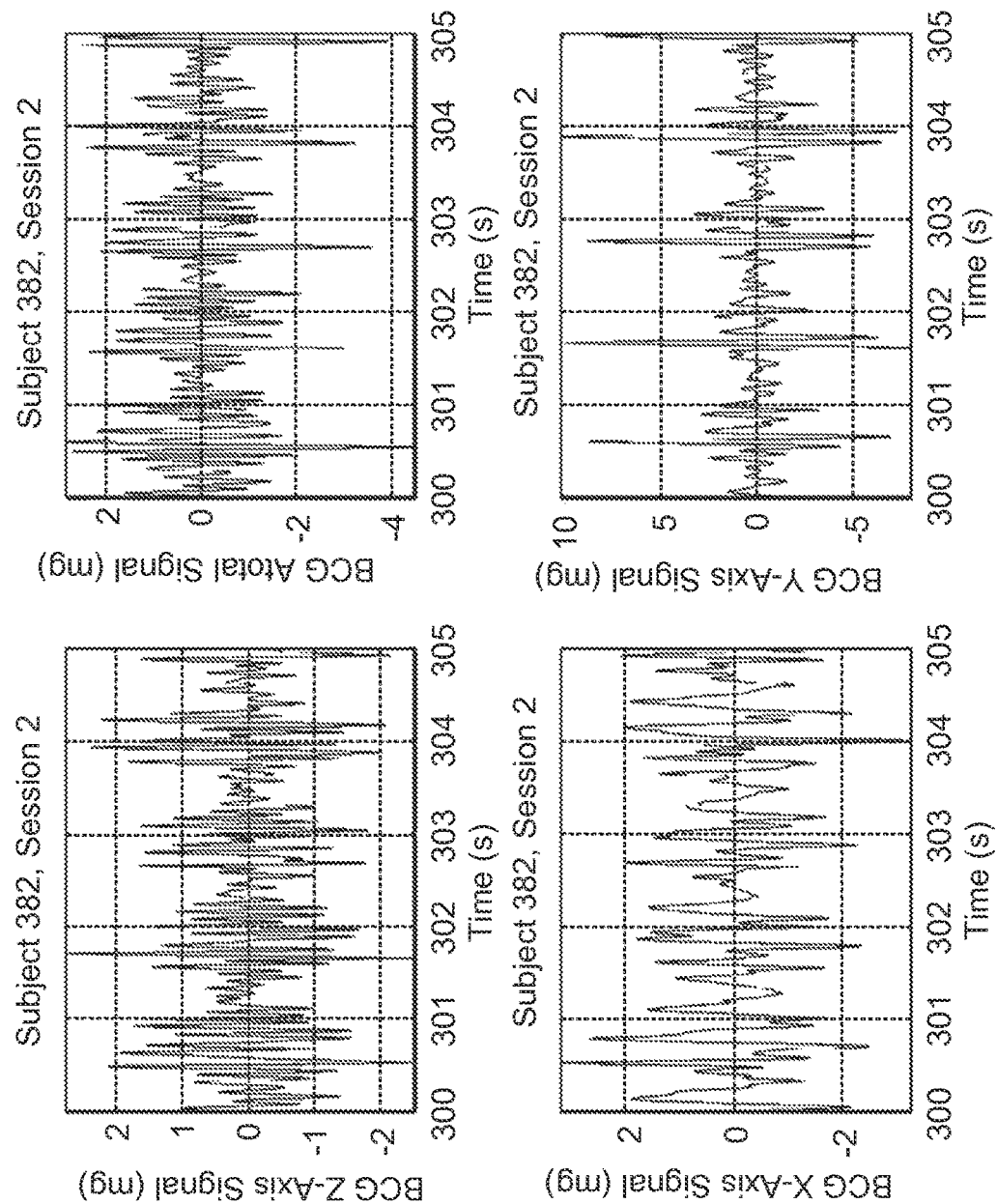
FIG. 8 shows x-axis acceleration, y-axis acceleration, z-axis acceleration, and vector-sum acceleration Ballisto-Cardiogram plots, in accordance with many embodiments.

FIG. 8 shows example x-axis acceleration, y-axis acceleration, z-axis acceleration, and vector-sum acceleration BCG plots measured using an accelerometer coupled to a wrist-worn device that is not held in contact with the subject's chest. These BCG plots show a different order with respect to which acceleration plots exhibit acceleration peaks corresponding to respective ejections of blood from the subject's left ventricle. Specifically, the y-axis acceleration BCG plot exhibits the most clear acceleration peaks corresponding to respective ejections of blood from the subject's left ventricle. The vector-sum acceleration (Atotal) BCG plot is the next most clear after the y-axis acceleration BCG plot. Finally, each of the x-axis acceleration and the z-axis acceleration BCG plots appear to be similarly exhibit the least clear acceleration peaks corresponding to respective ejections of blood from the subject's left ventricle. As is described herein with reference to FIG. 10, combinations of the component accelerations can be accomplished so as to exhibit greater signal variability, thereby having clearer acceleration peaks with respect to respective ejections of blood from the subject's left ventricle.

Figure 9:
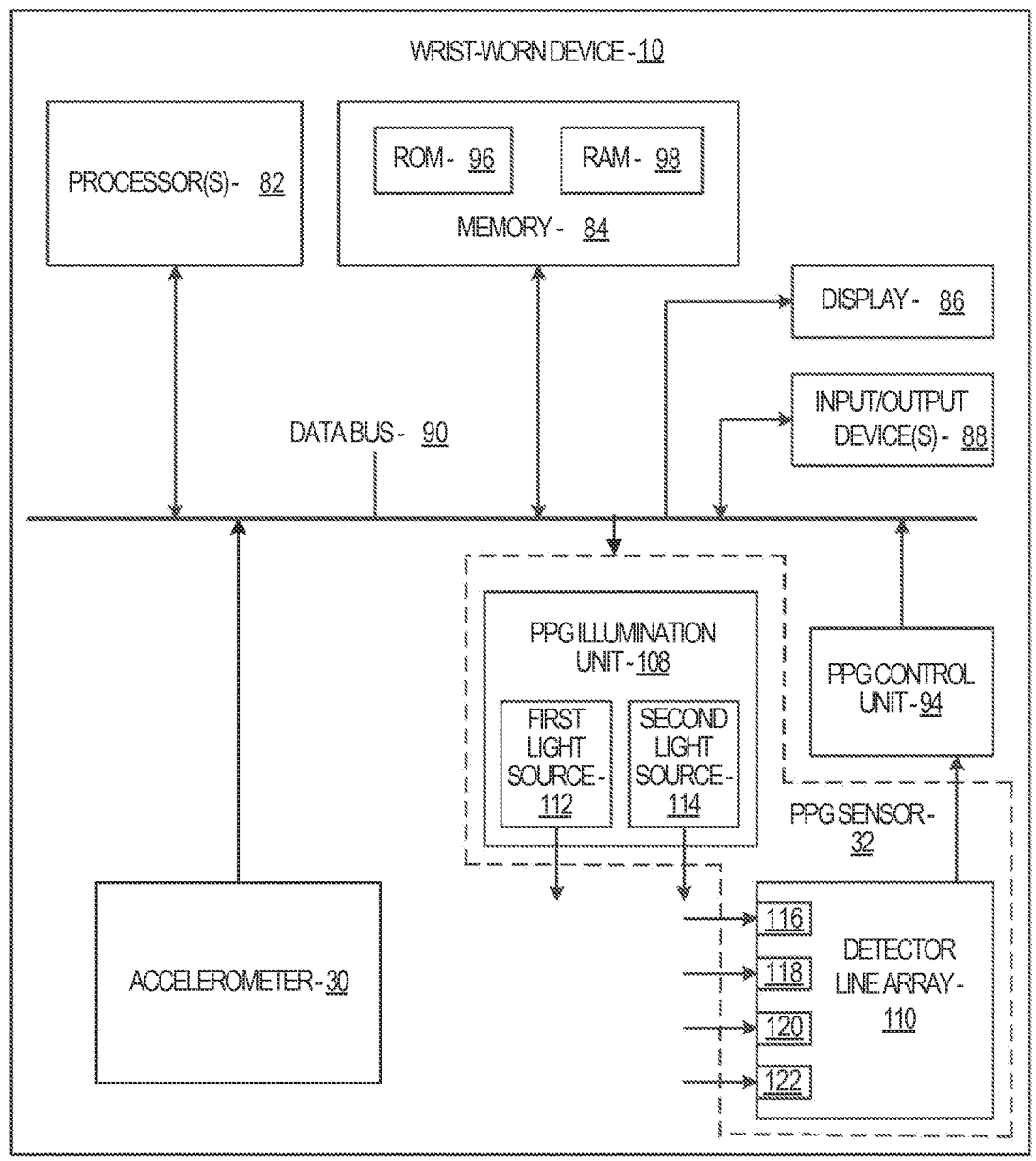
FIG. 9 is a schematic diagram of a wrist-worn blood-pressure measurement device, in accordance with many embodiments.

FIG. 9 schematically represents an embodiment of the wrist-worn device 10. In the illustrated embodiment, the wrist-worn device 10 includes one or more processors 82, memory 84, a display 86, one or more input/output devices 88, a data bus 90, the accelerometer 30, the PPG sensor 32, and a PPG sensor control unit 94. In many embodiments, the memory 84 includes read only memory (ROM) 96, and random access memory (RAM) 98. The one or more processors 82 can be implemented in any suitable form, including one or more field-programmable gate arrays (FPGA). The accelerometer 30 can be any suitable accelerometer (e.g., a three-axis low noise accelerometer).

The PPG sensor unit 64 includes a PPG illumination unit 108 and detector line array 110. The PPG illumination unit 108 includes two light sources 112, 114 which transmit light having different wavelengths onto the wrist. While any suitable wavelengths can be used, the first light source 112 generates a beam of light having a wavelength of 525 nm. The second light source 114 generates a beam of light having a wavelength of 940 nm. Any suitable number of light sources and corresponding wavelengths can be used and selected to provide desired variation in tissue penetrating characteristics of the light. The detector line array 110 can include any suitable number of light detectors. In many embodiments, the light detectors are disposed at a plurality of different distances from the light sources 112, 114 so that the detected light is associated with different mean penetration depths so as to enable detection of the arrival of the blood pressure pulse at different layers and/or within a layer of the wrist deeper than a layer sensed by a single light source and single detector PPG sensor. In the illustrated embodiment, the detector line array 110 includes four light detectors 116, 118, 120, 122, with each of the light detectors 116, 118, 120, 122 being disposed at a different distance from the light sources 112, 114. For example, the light detectors 116, 118, 120, 122 can be disposed at 2 mm, 3 mm, 4 mm, and 6 mm, respectively, from each of the light sources 112, 114. Signals generated by the light detectors 116, 118, 120, 122 are supplied to the PPG control unit 94, which includes an analog to digital converter to generate PPG sensor digital data that can be processed by the one or more processors 82 to determine the arrival of the blood pressure pulse to the wrist-worn device. The PPG control unit 94 controls activation of the light sources 112, 114, and can alternately illuminate the light sources 112, 114 at a frequency sufficiently high to enable combined assessment of the PPG sensor digital data generated by illumination of the wrist with the different wavelengths provided by the light sources 112, 114.

Measured acceleration data and the PPG sensor digital data can be transferred to, and stored in, the RAM 98 for any suitable subsequent use. For example, the data can be: 1) processed by the one or more processors 82 to determine PTTs and corresponding blood pressure values for the subject, 2) displayed on the display 86, and/or 3) output via the input/output devices 88 for any suitable purpose such as to a health care professional and/or a monitoring service. In many embodiments, the one or more processors 82 processes the acceleration data and PPG sensor digital data to generate trending data for a time period based on the one or more relative blood pressure values. Such trending data can be generated for any suitable time period, for example, for one or more days, one or more weeks, one or more months, and/or one or more years. One or more blood pressure values and/or associated trending data can be: 1) stored in the RAM 98, 2) displayed on the display 86, and/or 3) output via the input/output devices 88 for any suitable purpose such as to a health care professional and/or a monitoring service.

Figure 10:
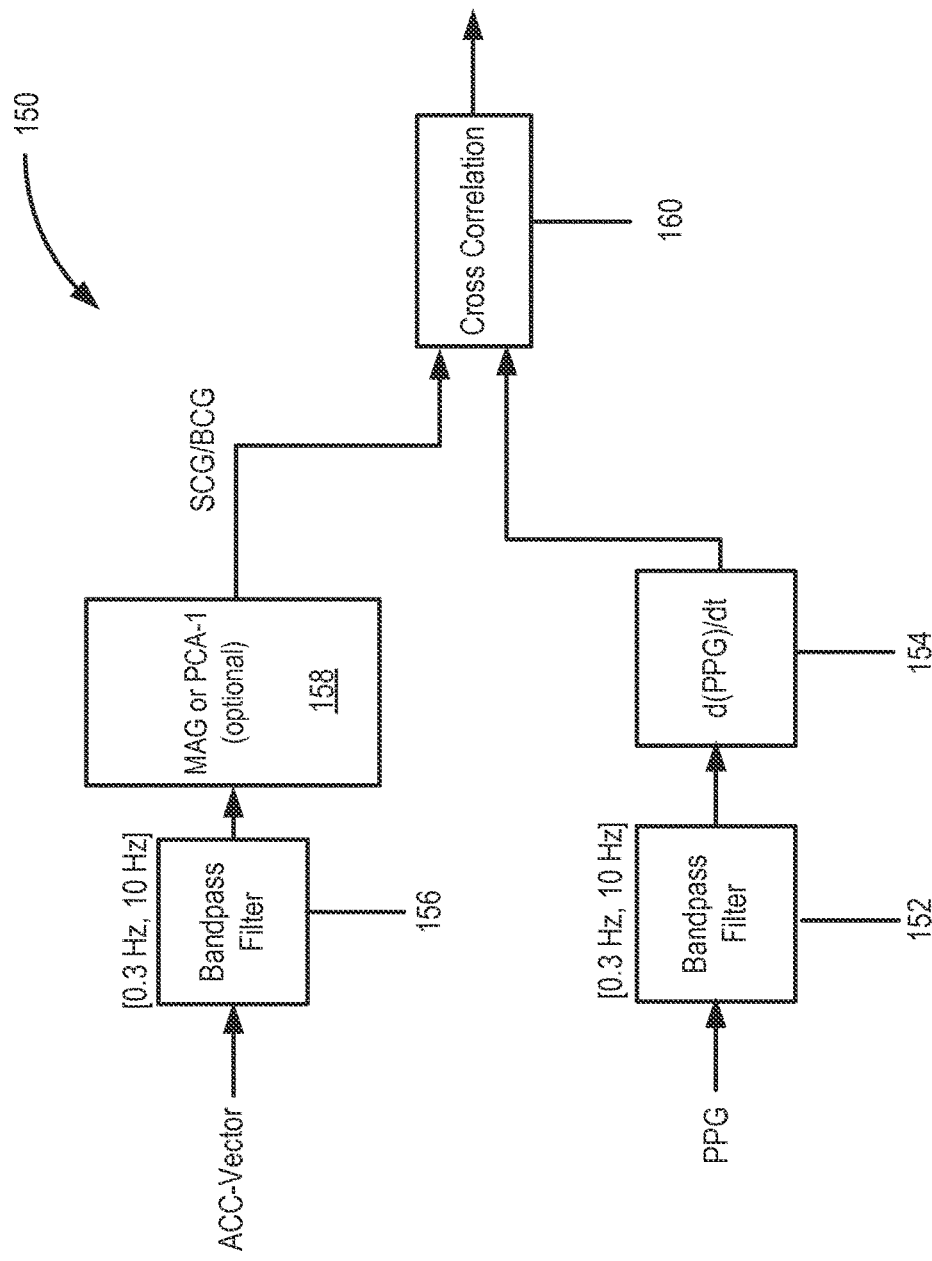
FIG. 10 is a schematic diagram of an approach for processing recorded acceleration data to identify when blood is ejected from the left ventricle of a user's heart, in accordance with many embodiments.

FIG. 10 illustrates an approach 150 for processing recorded acceleration data to identify when blood is ejected from the left ventricle of a user's heart, in accordance with many embodiments. In the approach 150, output from the PPG sensor 32 is processed with a suitable bandpass filter 152 (e.g., a bandpass filter that attenuates frequencies less than 0.3 Hz and frequencies greater than 10 Hz) to reduce noise. The filtered PPG sensor output is then differentiated with respect to time (act 154) so as to produce a signal that more clearly exhibits when the blood pressure pulse first arrives to the wrist prior to the arrival to the wrist of a reflection of the blood pressure pulse. In a similar fashion, the output from the accelerometer 30 (three component acceleration vector data, which varies over time) is also processed with a suitable bandpass filter 156 (e.g., a bandpass filter that attenuates frequencies less than 0.3 Hz and frequencies greater than 10 Hz) to reduce noise. The filtered acceleration vector data is then selectively combined so that the combined acceleration values exhibit greater variability with respect to ejections of blood from the subject's left ventricle, thereby exhibiting clearer acceleration peaks corresponding to respective ejections of blood from the subject's left ventricle. In one variation of the approach 150, a magnitude trace is calculated from the three component acceleration vector data (act 158). As illustrated in FIGS. 7 and 8 for each of the vector-sum acceleration data plots (Atotal) for both SCG and BCG, such a magnitude trace can exhibit clear acceleration magnitude peaks corresponding to respective ejections of blood from the subject's left ventricle. In another variation of the approach 150, a principal component analysis (PCA) can be performed (act 158) to identify a linear combination of the three components of the acceleration data that exhibits maximum acceleration variability, thereby increasing the likelihood that the identified combination will exhibit clear acceleration magnitude peaks corresponding to respective ejections of blood from the subject's left ventricle while allowing for flexibility in accelerometer orientation on the wrist. The principal component analysis can be accomplished by calculating the three-dimensional eigenvector associated with the maximum eigenvalue of the covariance matrix of the measured acceleration vector samples within a time window. The components of this eigenvector are used as the coefficients in the linear combination PCA-1 of the acceleration components. The resulting linear combination time samples can then be evaluated to identify peaks corresponding to respective ejections of blood from the subject's left ventricle. The PCA procedure is repeated for subsequent time windows of interest that contain measured acceleration data. In act 160, identified time points for the arrival of blood pressure pulses to the wrist are correlated with respective time points for the ejection of blood from the user's left ventricle (i.e., acceleration peaks identified in the combination of the three component acceleration vector data). For example, each time point for the arrival of a blood pressure pulse can be correlated with a respective time point for the ejection of blood from the left ventricle that falls within a preselected preceding time period (e.g., from 100 ms to 300 ms prior to the arrival of the blood pressure pulse to the wrist. Any suitable preceding time period can be used. And the preceding time period used can be customized to a particular subject to reflect individual variations in pulse wave velocity related characteristics, such as relative differences in arterial stiffness.

Figure 11:
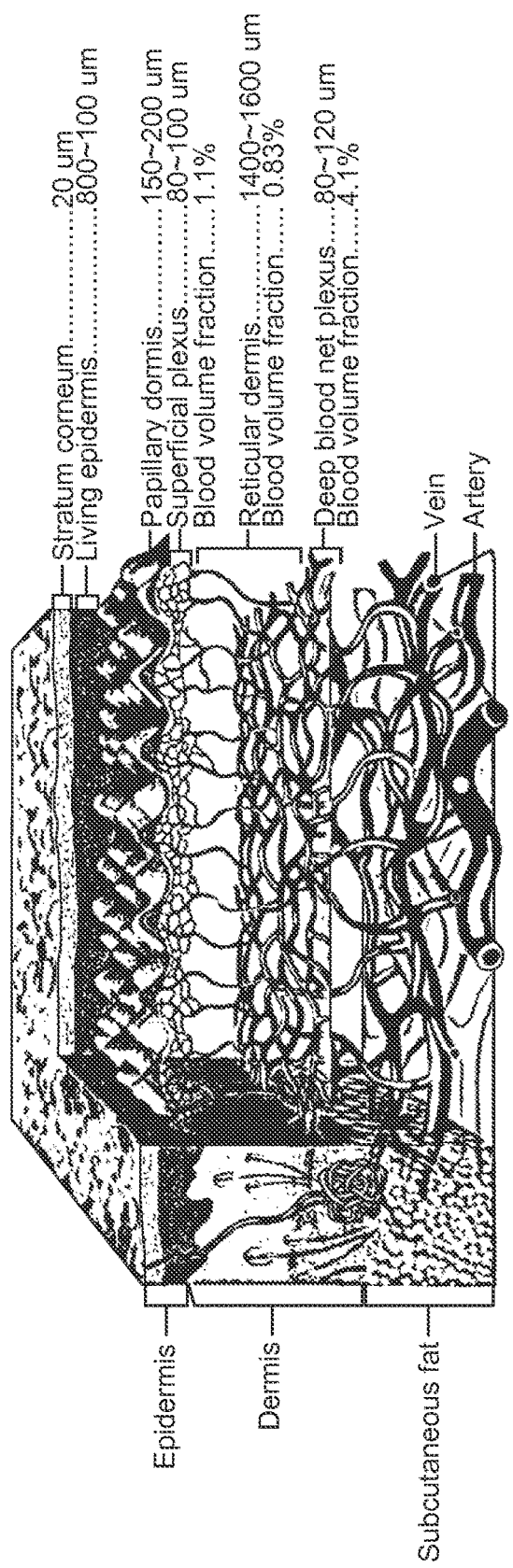
FIG. 11 illustrates subsurface layers of a subject.

FIG. 11 illustrates subsurface layers of a subject. The illustrated layers include: 1) the stratum corneum (about 200 µm thick), 2) the living epidermis (80 to 100 µm thick), 3) the papillary dermis (150 to 200 µm thick), 4) the superficial plexus (80 to 100 µm thick with a blood volume fraction of about 1.1%), 5) the reticular dermis (1400 to 1600 µm thick with a blood volume faction of about 0.83%), and 6) the deep blood net plexus (80 to 120 µm thick with a blood volume fraction of about 4.1%). Upon arrival to the wrist, the blood pressure pulse arrives at the deep blood net plexus layer before propagating to the overlying layers. As vasomotion (vasodilation and vasoconstriction) plays an important role in regulating blood flow in arterioles and capillaries further downstream in the arterial tree, using the PPG sensor to detect the arrival of the blood pressure pulse in the deep blood net plexus layer may increase the strength of the correlation between blood pressure and PTT by reducing vasomotion induced variability of PTT in shallower layers more subject to vasomotion induced variation in pulse wave velocity of the blood pressure pulse.

Figure 12:
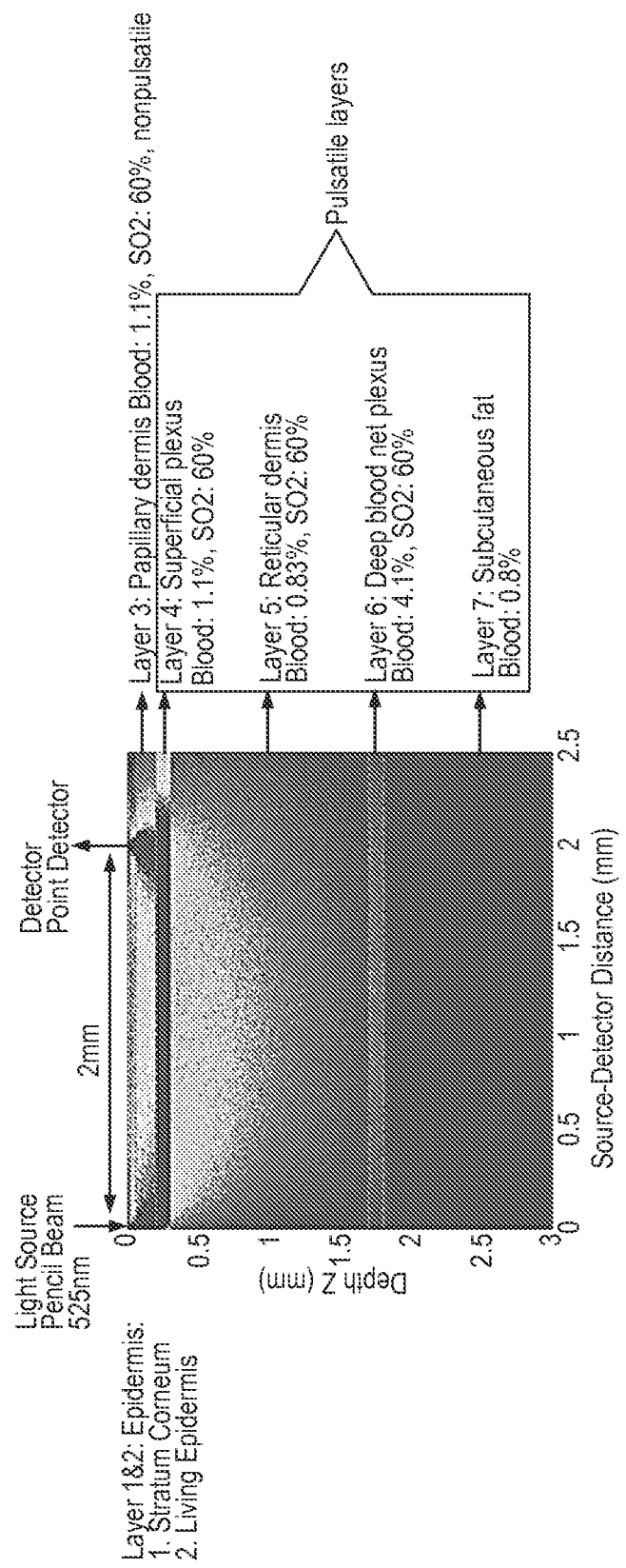
FIGS. 12 through 14 illustrate detection of different mean penetration depths of light emitted by a PPG sensor having returning light detectors disposed at different distances from each of two light sources of the PPG sensor, in accordance with many embodiments.
Figure 13:
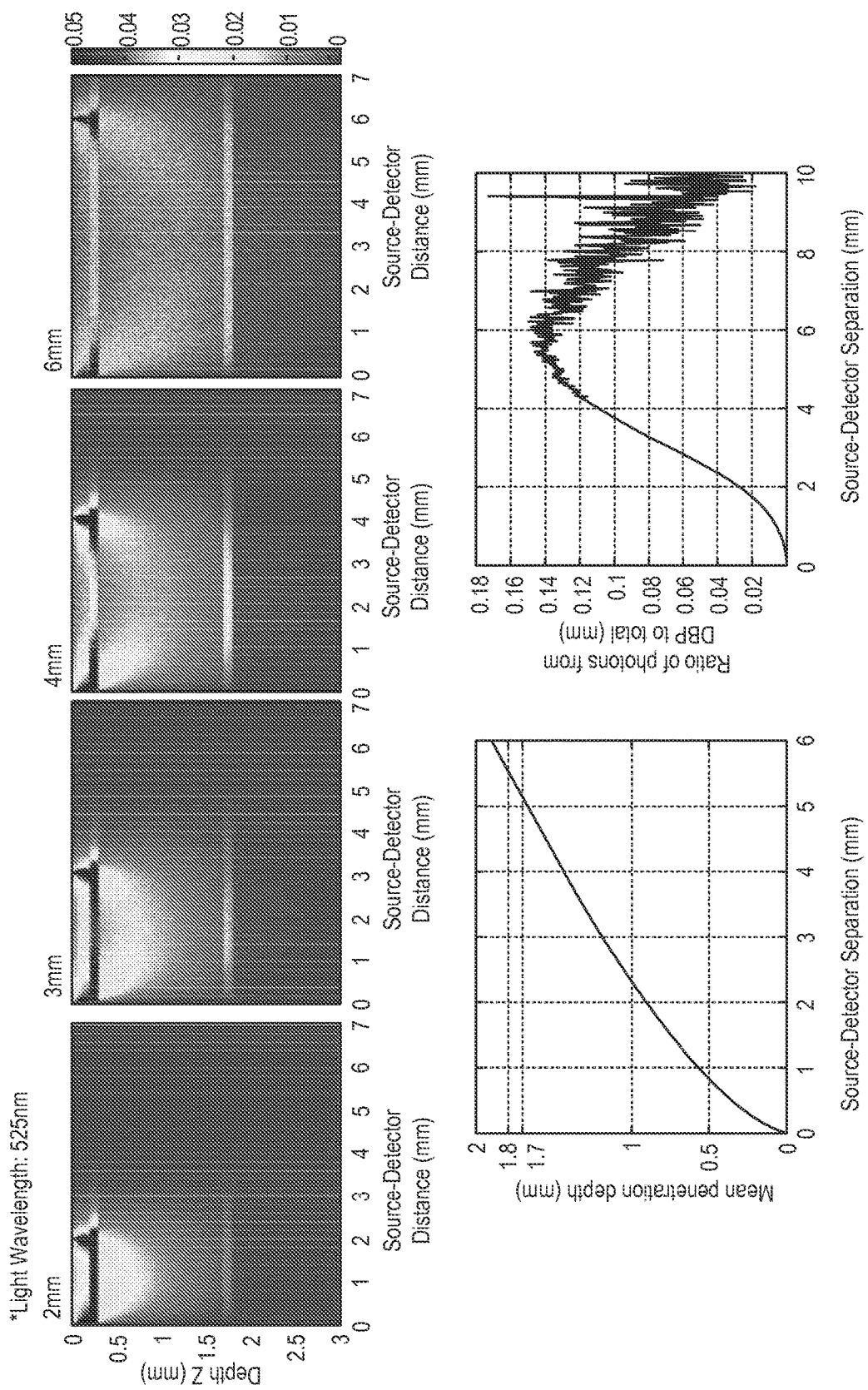
Figure 14:
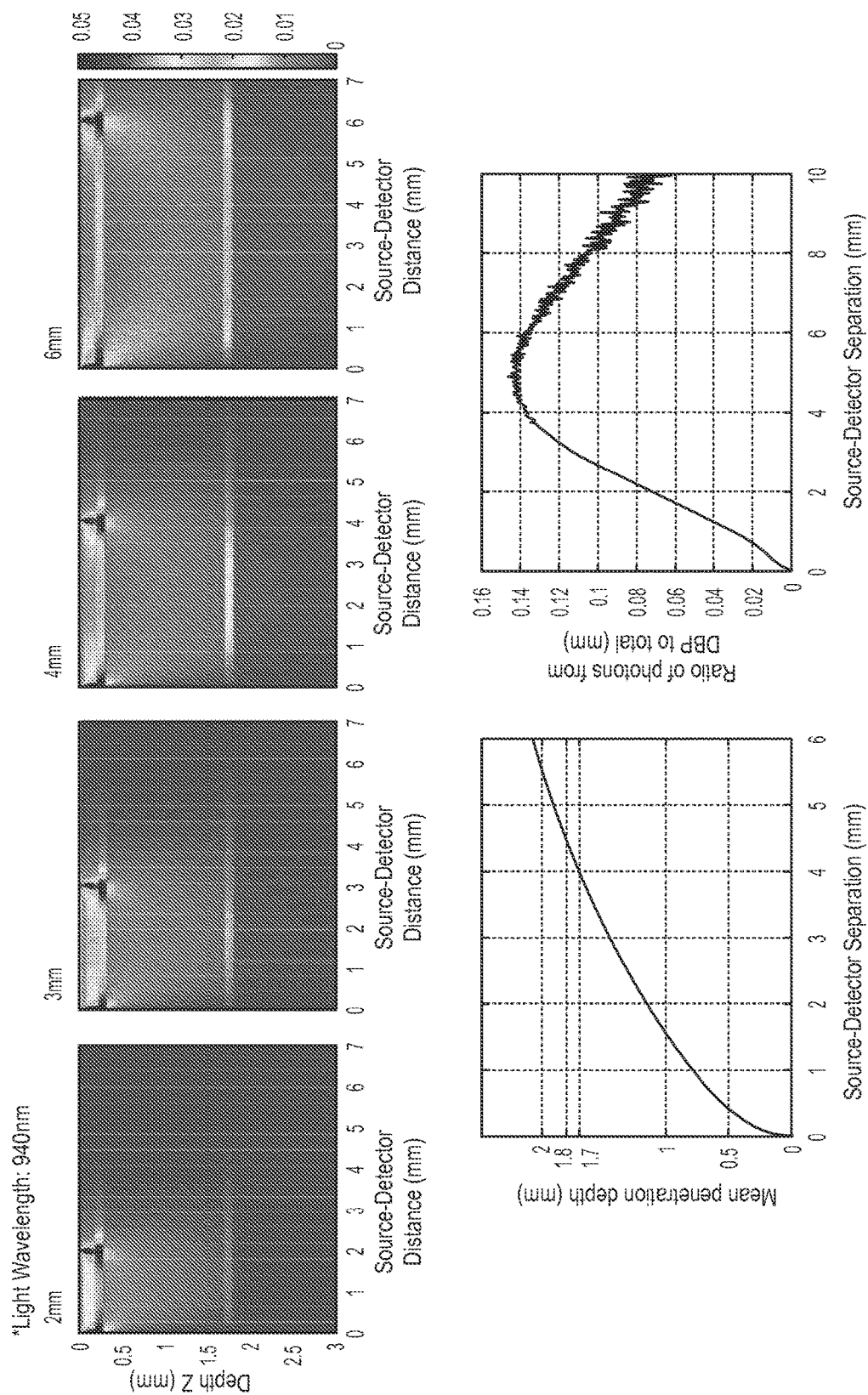
Figure 15:
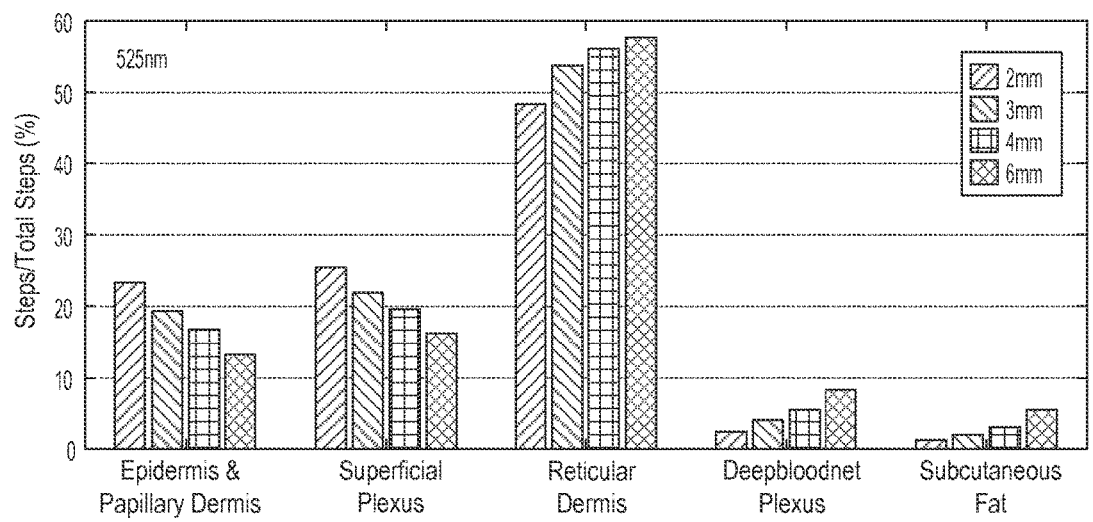
FIGS. 15 and 16 show relative contribution by subsurface layer to returning light detected by the light detectors disposed at different distances for two different light source wavelengths, in accordance with many embodiments.
Figure 16:
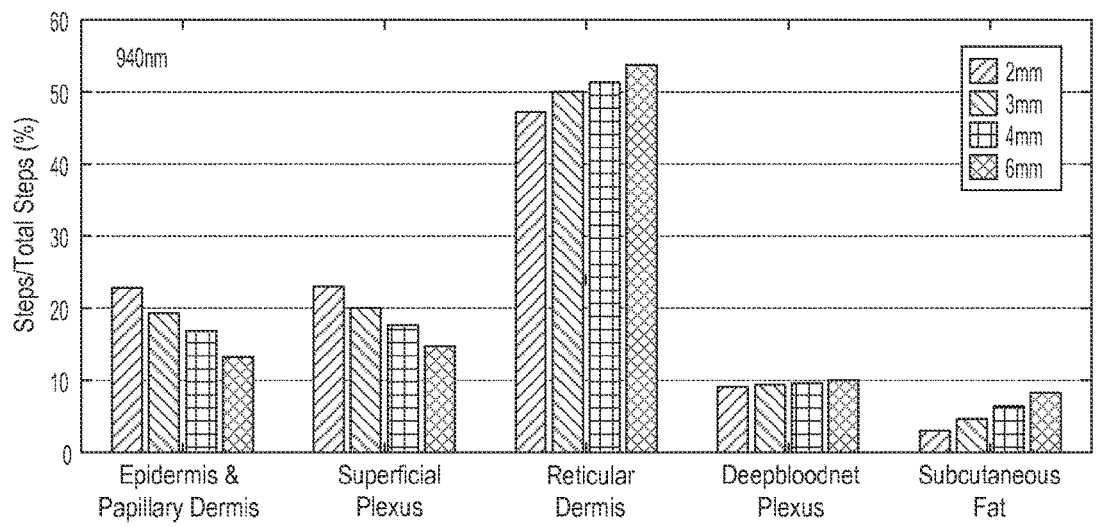
Figure 17:
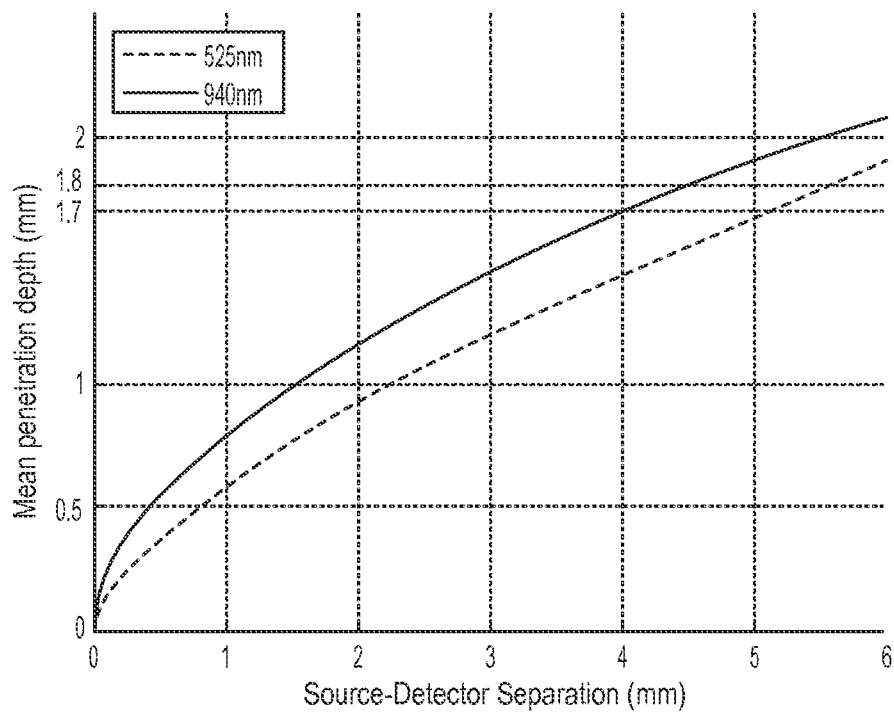
FIG. 17 illustrates variation of mean penetration depth as a function of source-detector separation for two different source light wavelengths, in accordance with many embodiments.
Figure 18:
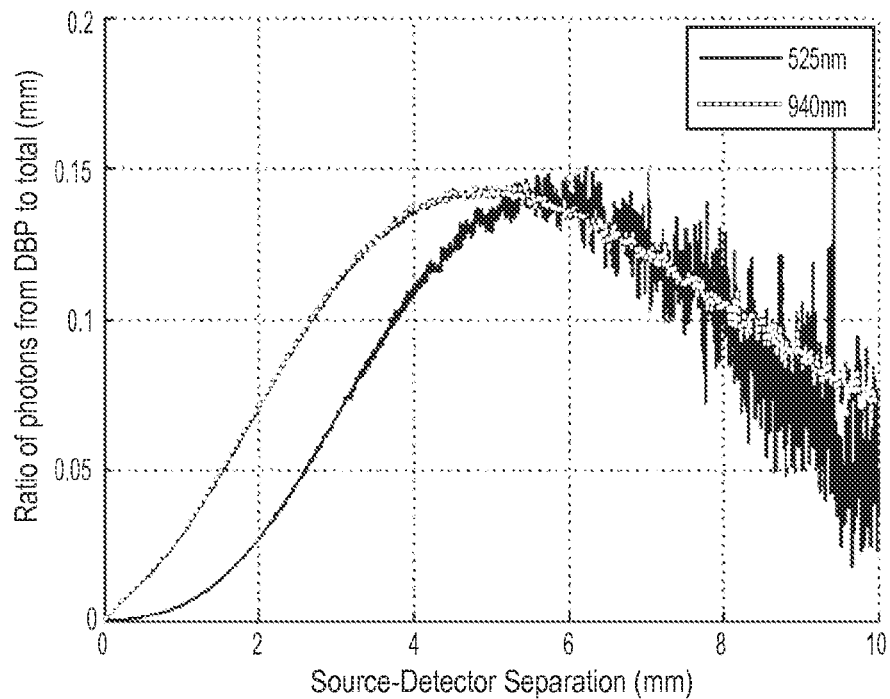
FIG. 18 illustrates variation of the ratio of photons from the deep blood plexus (DBP) layer as a function of source-detector separation for two different source light wavelengths, in accordance with many embodiments.

FIGS. 12 through 14 illustrate detection of different mean penetration depths of light emitted by a PPG sensor having returning light detectors disposed at different distances from each of two light sources of the PPG sensor, in accordance with many embodiments. FIG. 12 illustrates distribution of sensing depths for a combination of a 525 nm light source and a point detector disposed 2 mm from the 525 nm light source. FIG. 13 illustrates distributions of sensing depths for the combination of a 525 nm light source and point detectors disposed at 2 mm, 3 mm, 4 mm, and 6 mm from the 525 nm light source, as well as corresponding graphs of mean penetration depth and ratio of photons from the deep blood net plexus layer to the total detected returned light as a function of source-detector separation. FIG. 14 illustrates distributions of sensing depths for the combination of a 940 nm light source and point detectors disposed at 2 mm, 3 mm, 4 mm, and 6 mm from the 940 nm light source, as well as corresponding graphs of mean penetration depth and ratio of photons from the deep blood net plexus layer to the total detected returned light as a function of source-detector separation. FIGS. 15 and 16 show contribution of the total detected returned light for each layer for each wavelength and source-detector separation. FIGS. 17 and 18 show combined graphs corresponding to the graphs of FIGS. 13 and 14.

Using the data illustrated in FIGS. 12 through 18, the signals from the detectors 116, 118, 120, 122 generated for each of the light wavelengths generated by the light sources 112, 114 can be processed to detect arrival of the blood pressure pulse within a selected layer (e.g., with the deep blood net plexus layer). For example, arrival of the blood pressure pulse within the reticular dermis layer can be detected first due to the large percentage of the returning light incident on the detectors 116, 118, 120, 122 that returns from the reticular dermis layer. Once the arrival time to the reticular dermis layer is determined, the signals during a suitable time interval prior to the arrival time to the reticular dermis layer can be combined and/or processed to focus attention on detecting the earlier arrival of the blood pressure pulse to the deep blood plexus layer. Typically, infrared (e.g., 940 nm wavelength) light penetrates deeper into the skin compared to visible light such as green (e.g., 525 nm wavelength) or red (e.g., 660 nm wavelength). Hence, a PPG waveform recorded from infrared light corresponds to light reflected from deeper blood vessels, while a PPG waveform recorded from green light corresponds to light reflected from capillaries near the skin surface. Since the blood pulse arrives at deeper blood vessels earlier than capillaries near the skin surface, the blood pulse appears in the infrared PPG before the green PPG at the same location (e.g., on the wrist). A cross correlation of infrared and green PPG signals can be used to determine the relative delay between the arrival of the blood pulse at deeper blood vessels and the arrival of the blood pulse at capillaries near the skin surface.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for determining a pressure of blood within a cardiovascular system of a user, the cardiovascular system including a heart and the user having a wrist covered by skin, the method comprising:
    detecting, with an accelerometer of a wrist-worn device non-invasively engaging an anterior surface of the wrist of the user, a first signal indicative of when blood is ejected from the left ventricle of the user's heart;
    detecting, with a PPG or a pulse pressure sensor of the wrist-worn device non-invasively engaging the skin on the wrist of the user, a second signal indicative of when a blood pressure pulse corresponding to the blood ejection arrives at the wrist;
    storing acceleration data corresponding an output of the accelerometer for a recording time period;
    using the second signal to select a candidate time period within the recording time period to select the acceleration data to evaluate to identify when the blood election from the user's left ventricle occurred corresponding to the blood pressure pulse;
    calculating a pulse transit time (PTT) for the blood pressure pulse from the ejection of the blood from the left ventricle to arrival of the blood pressure pulse at the wrist; and
    generating one or more relative blood pressure values for the user based on the PTT.

2. The method of claim 1, comprising detecting when the accelerometer is positioned on the user's chest.

3. The method of claim 1, comprising:
    based on evaluation of the output of the accelerometer, identifying two or more candidate times for when the blood ejection from the left ventricle occurred within the candidate time period; and
    selecting one of the candidate times closest to a target time within the candidate time period for the PTT calculation.

4. The method of claim 1, wherein the candidate time period is from about 100 ms to about 300 ms before a detected time when the pulse arrives at the user's wrist.

5. The method of claim 1, comprising processing an output of the accelerometer with a bandpass filter to remove noise.

6. The method of claim 5, wherein the bandpass filter attenuates frequencies less than about 0.3 Hz and greater than about 10 Hz.

7. The method of claim 1, comprising processing the PPG or pressure sensor output with a bandpass filter to remove noise.

8. The method of claim 7, wherein the bandpass filter attenuates frequencies less than about 0.3 Hz and greater than about 10 Hz.

9. The method of claim 1, comprising:
    differentiating the PPG or pressure sensor signal with respect to time; and
    evaluating the differentiated signal to select a time of arrival of the pressure pulse at the wrist prior to arrival of a reflection of the blood pressure pulse at the wrist.

10. The method of claim 1, wherein an output of the accelerometer comprises accelerations measured in three directions, and the method further comprises:
    calculating combined acceleration magnitude values from the measured accelerations, the combined acceleration magnitudes values being based on a combination of the measured acceleration in at least two directions; and
    processing the combined acceleration magnitude values to detect when blood is ejected from the left ventricle of the user's heart.

11. The method of claim 10, comprising performing an eigenvector-based principle component analysis of the measured accelerations to calculate the combined acceleration magnitude values so as to reflect increased sensitivity to blood ejections from the left ventricle.

12. The method of claim 1, further comprising processing output from the PPG sensor to determine a tone of blood vessels of the user, and wherein the one or more blood pressure values generated for the user is further based on the determined tone of the blood vessels of the user.

13. The method of claim 1, wherein the generation of the one or more blood pressure values is further based on calibration data including measured blood pressure values and corresponding PTTs for the user.

14. The method of claim 1, further comprising calculating trending data for a time period based on the one or more relative blood pressure values.

15. The method of claim 14, wherein the time period comprises one or more days, one or more weeks, one or more months, or one or more years.

16. The method of claim 1, further comprising transmitting the one or more relative blood pressure measurements to a mobile device, table, computer, or database.

17. The method of claim 1, further comprising detecting different mean penetration depths of light emitted by the PPG sensor by at least one of: a) using at least two light detectors disposed at different distances from a light source of the PPG sensor; and b) using a plurality of light sources configured to emit different wavelengths of light.

18. The method of claim 17, further comprising using at least two different mean penetration depths to evaluate light returned from a deeper penetration depth relative to the two different mean penetration depths.

19. The method of claim 17, comprising processing one or more signals from the PPG sensor to detect when the blood pressure pulse corresponding to the ejected blood arrives at the deep blood plexus (DBP) layer at the user's wrist.

20. The method of claim 17, comprising processing one or more signals from the PPG sensor to detect when the blood pressure pulse corresponding to the ejected blood arrives at the user's wrist within a radial artery of the user.

21. The method of claim 17, comprising processing one or more signals from the PPG sensor to determine a tone of blood vessels of the user, and wherein the one or more blood pressure values generated for the subject is further based on the determined tone of the blood vessels of the user.

22. The method of claim 1, wherein generating the one or more relative blood pressure values for the user based on the PTT comprises:
generating an estimated elevation difference between the wrist-worn device and the user's heart; and
using the estimated elevation difference to account for hydrostatic elevation differences in blood pressure within the user.

23. The method of claim 22, wherein the estimated elevation difference between the wrist-worn device and the user's heart is generated based on output from one or more pressure sensors or an estimated arm posture derived from an output of the accelerometer.

* * * * *

UNITED STATES PATENT AND TRADEMARK OFFICE
CERTIFICATE OF CORRECTION

PATENT NO.         : 10,517,489 B2
APPLICATION NO.    : 15/507607
DATED              : December 31, 2019
INVENTOR(S)        : Ravi Narasimhan et al.

Page 1 of 1

It is certified that error appears in the above-identified patent and that said Letters Patent is hereby corrected as shown below:

In the Claims
Column 16, Claim 1, Line 10: delete "blood election" and insert --blood ejection--.

Signed and Sealed this
Twenty-sixth Day of May, 2020

Andrei Iancu
*Director of the United States Patent and Trademark Office*